US009846168B2

(12) United States Patent
Gee et al.

(10) Patent No.: US 9,846,168 B2
(45) Date of Patent: Dec. 19, 2017

(54) FLUORESCENT METAL ION INDICATORS WITH LARGE STOKES SHIFTS

(71) Applicant: LIFE TECHNOLOGIES CORPORATION, Carlsbad, CA (US)

(72) Inventors: Kyle Gee, Springfield, OR (US); Vladimir Martin, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 15/152,346

(22) Filed: May 11, 2016

(65) Prior Publication Data

US 2016/0305964 A1    Oct. 20, 2016

Related U.S. Application Data

(60) Division of application No. 14/307,445, filed on Jun. 17, 2014, now Pat. No. 9,372,181, which is a division
(Continued)

(51) Int. Cl.
*G01N 21/76* (2006.01)
*G01N 33/84* (2006.01)
(Continued)

(52) U.S. Cl.
CPC .......... *G01N 33/84* (2013.01); *C07C 229/18* (2013.01); *C07C 311/44* (2013.01);
(Continued)

(58) Field of Classification Search
CPC ... C07C 229/18; C07C 311/44; C07D 209/14; C07D 221/14; C07D 265/38;
(Continued)

(56) References Cited

U.S. PATENT DOCUMENTS 4,520,110 A    5/1985 Stryer et al.
4,542,104 A    9/1985 Stryer et al.
(Continued)

FOREIGN PATENT DOCUMENTS

WO    WO97/39064    10/1997
WO    WO-2006/023231    3/2006

OTHER PUBLICATIONS

Brinkley, , "A Brief Survey of Methods for Preparing Protein Conjugates with Dyes, Haptens, and Cross-Linking Reagents", *Bioconjugate Chemistry*, vol. 3, No. 1, 1992, 2-13.
(Continued)

*Primary Examiner* — Robert Xu

(57) ABSTRACT

The present invention provides fluorogenic compounds for the detection of target metal ions wherein the compounds exhibit a Stokes shift greater than 50 nm and the detectable signal is modulated by photoinduced electron transfer (PET). The present compounds consist of three functional elements, the ion sensing moiety (chelating moiety), the reporter moiety (fluorophore or fluorescent protein) and spacer or linker between the sensing and reporter moieties of the present compound that allows for PET upon binding of a metal ion and excitation by an appropriate wavelength.

12 Claims, 3 Drawing Sheets

Related U.S. Application Data of application No. 13/194,727, filed on Jul. 29, 2011, now Pat. No. 8,785,208, which is a continuation of application No. 12/651,138, filed on Dec. 31, 2009, now abandoned, which is a continuation of application No. 12/484,903, filed on Jun. 15, 2009, now abandoned, which is a continuation of application No. 12/180,273, filed on Jul. 25, 2008, now abandoned, which is a continuation of application No. 11/191,799, filed on Jul. 27, 2005, now abandoned.

(60) Provisional application No. 60/591,750, filed on Jul. 27, 2004.

(51) Int. Cl.

| | | |
|---|---|---|
| C07C 229/18 | (2006.01) | |
| C07D 221/14 | (2006.01) | |
| C07D 265/38 | (2006.01) | |
| C07D 311/82 | (2006.01) | |
| C09B 5/60 | (2006.01) | |
| C09B 5/62 | (2006.01) | |
| C09B 11/06 | (2006.01) | |
| C09K 11/06 | (2006.01) | |
| C07D 209/14 | (2006.01) | |
| C07D 311/90 | (2006.01) | |
| G01N 33/20 | (2006.01) | |
| C07C 311/44 | (2006.01) | |
| C07K 14/195 | (2006.01) | |
| C07K 14/435 | (2006.01) | |
| C09B 11/08 | (2006.01) | |
| C09B 19/00 | (2006.01) | |
| C09B 57/08 | (2006.01) | |
| C07D 413/04 | (2006.01) | |

(52) U.S. Cl.
CPC ......... *C07D 209/14* (2013.01); *C07D 221/14* (2013.01); *C07D 265/38* (2013.01); *C07D 311/82* (2013.01); *C07D 311/90* (2013.01); *C07K 14/195* (2013.01); *C07K 14/43595* (2013.01); *C09B 5/60* (2013.01); *C09B 5/62* (2013.01); *C09B 11/06* (2013.01); *C09B 11/08* (2013.01); *C09B 19/00* (2013.01); *C09B 19/005* (2013.01); *C09B 57/08* (2013.01); *C09K 11/06* (2013.01); *G01N 33/20* (2013.01); *C07D 413/04* (2013.01); *C09K 2211/1014* (2013.01); *G01N 2458/00* (2013.01)

(58) Field of Classification Search
CPC .. C07D 311/82; C07D 311/90; C07D 413/04; C07K 14/195; C07K 14/43595; C09B 11/06; C09B 11/08; C09B 19/00; C09B 19/005

See application file for complete search history.

(56) References Cited

U.S. PATENT DOCUMENTS

| | | |
|---|---|---|
| 4,603,209 A | 7/1986 | Tsien et al. |
| 4,711,955 A | 12/1987 | Ward et al. |
| 4,774,339 A | 9/1988 | Haugland et al. |
| 4,810,636 A | 3/1989 | Corey et al. |
| 4,812,409 A | 3/1989 | Babb et al. |
| 4,849,362 A | 7/1989 | Demarinis et al. |
| 4,859,582 A | 8/1989 | Stryer et al. |
| 4,945,171 A | 7/1990 | Haugland et al. |
| 5,047,519 A | 9/1991 | Hobbs et al. |
| 5,049,673 A | 9/1991 | Tsien et al. |
| 5,055,556 A | 10/1991 | Stryer et al. |
| 5,132,432 A | 7/1992 | Haugland et al. |
| 5,187,288 A | 2/1993 | Kang et al. |
| 5,227,487 A | 7/1993 | Haugland et al. |
| 5,242,805 A | 9/1993 | Naleway et al. |
| 5,248,782 A | 9/1993 | Haugland et al. |
| 5,268,486 A | 12/1993 | Waggoner et al. |
| 5,274,113 A | 12/1993 | Kang et al. |
| 5,352,803 A | 10/1994 | Mattingly |
| 5,362,628 A | 11/1994 | Haugland et al. |
| 5,433,896 A | 7/1995 | Kang et al. |
| 5,442,045 A | 8/1995 | Haugland et al. |
| 5,451,343 A | 9/1995 | Neckers et al. |
| 5,453,517 A | 9/1995 | Kuhn et al. |
| 5,459,276 A | 10/1995 | Kuhn et al. |
| 5,486,616 A | 1/1996 | Waggoner et al. |
| 5,501,980 A | 3/1996 | Katerinopoulos et al. |
| 5,516,864 A | 5/1996 | Kuhn |
| 5,516,911 A | 5/1996 | London et al. |
| 5,569,587 A | 10/1996 | Waggoner |
| 5,569,766 A | 10/1996 | Waggoner et al. |
| 5,573,904 A | 11/1996 | Mattingly |
| 5,627,027 A | 5/1997 | Waggoner |
| 5,656,554 A | 8/1997 | Desai et al. |
| 5,696,157 A | 12/1997 | Wang et al. |
| 5,714,327 A | 2/1998 | Houthoff et al. |
| 5,773,227 A | 6/1998 | Kuhn et al. |
| 5,798,276 A | 8/1998 | Haugland et al. |
| 5,800,996 A | 9/1998 | Lee et al. |
| 5,830,912 A | 11/1998 | Gee et al. |
| 5,846,737 A | 12/1998 | Kang |
| 5,847,162 A | 12/1998 | Lee et al. |
| 5,863,727 A | 1/1999 | Lee et al. |
| 5,945,526 A | 8/1999 | Lee et al. |
| 6,008,373 A | 12/1999 | Waggoner et al. |
| 6,008,379 A | 12/1999 | Benson et al. |
| 6,017,712 A | 1/2000 | Lee et al. |
| 6,025,505 A | 2/2000 | Lee et al. |
| 6,048,982 A | 4/2000 | Waggoner et al. |
| 6,080,852 A | 6/2000 | Lee et al. |
| 6,124,135 A | 9/2000 | Leiner et al. |
| 6,130,101 A | 10/2000 | Mao et al. |
| 6,140,494 A | 10/2000 | Hamilton et al. |
| 6,162,931 A | 12/2000 | Gee et al. |
| 6,172,188 B1* | 1/2001 | Thastrup .......... C07K 14/43595 435/325 |
| 6,184,379 B1 | 2/2001 | Josel et al. |
| 6,221,606 B1 | 4/2001 | Benson et al. |
| 6,229,055 B1 | 5/2001 | Klaubert et al. |
| 6,239,271 B1 | 5/2001 | Rabbani et al. |
| 6,335,440 B1 | 1/2002 | Lee et al. |
| 6,339,392 B1 | 1/2002 | Ashihara et al. |
| 6,348,599 B1 | 2/2002 | Cummins et al. |
| 6,358,684 B1 | 3/2002 | Lee |
| 6,359,135 B1 | 3/2002 | Vasudevan et al. |
| 6,372,445 B1 | 4/2002 | Davis et al. |
| 6,403,807 B1 | 6/2002 | Singh et al. |
| 6,562,632 B1 | 5/2003 | Szalecki et al. |
| 6,664,047 B1 | 12/2003 | Haugland et al. |
| 6,716,979 B2 | 4/2004 | Diwu et al. |
| 6,974,873 B2 | 12/2005 | Leung et al. |
| 6,977,305 B2 | 12/2005 | Leung et al. |
| 2009/0029389 A1 | 1/2009 | Gee et al. |
| 2010/0196922 A1 | 8/2010 | Gee |

OTHER PUBLICATIONS

De Silva, A. Prasanna et al., "Proof-of-Principle of Molecular-Scale Arithematic", *Journal of the American Chemical Society*, 122, 2000, 3965-3966.

De Silva, A. Prasanna et al., "Sinaling Recognition Events with Fluoresent Sensors and Switches", *Chem. Rev.*, vol. 97, 1997, 1515-1566.

Furniss, Brian S. et al., "Resolution of Racemates", *Vogel's Textbook of Practical Organic Chemistry*, Fifth Ed, Longman Group UK Ltd., Essex, 1989, 809-816.

Haugland, "Molecular Probes Handbook of Fluorescent Probes and Research Products", 9th Edition, 2002 (CD-ROM Format), *Molecular Probes*, 2002.

(56) References Cited

OTHER PUBLICATIONS

He, Huarui et al., "A fluorescent Chemosensor for Sodium Based on Photoinduced Electron Transfer,", *J. Am. Chem. Soc. vol. 75, No. 3*,, Feb. 1, 2003, pp. 549-555.

He, Huarui et al., "A Fluorescent Sensor with High Selectivity and Sensitivity for Potassium in Water", *J. Am. Chem Soc.*, vol. 125, 2003, 1468-1469.

Heller, A., "Electrical Wiring of Redox Enzymes", *Acc. Chem. Res.*, vol. 23, No. 5, 1990, 128-134.

Ji, H. et al., "Spacer Length Effect on the Photoinduced Electron Transfer Fluorescent Probe for Alkali Metal Ions", *Photochemistry and Photobiology*, 69(5), 1999, 513-516.

Kuban, Petr et al., "Vertically Stratified Flows in Microchannels. Computational Simulations and Applications to Solvent Extraction and Ion Exchange", *Anal. Chem*, vol. 75, No. 14, Jul. 15, 2003, 3549-3556.

Raju, B. et al., "A fluorescent indicator for measuring cytosolic free magnesium", *Am. J. Physiol.*, vol. 256, 1989, C540-C548.

Sandler, et al., "Organic Functional Group Preparations: Volume 3", Academic Press, San Diego, 1989, 1-552.

Silva, A. et al., "Proof-of-Principle of Molecular-Scale Arithmetic", *J. Am. Chem. Soc.*, 2000, pp. 3965-3966.

Spatola, et al., "Ch 5: Peptide Backbone Modifications: A Structure-Activity Analysis of Peptides Containing Amide Bond Surrogates, Conformational Constraints, and Rela", *Chemistry and Biochemistry of Amino Acids, Peptides and Proteins*, vol. 7, 1983, 267-357.

WO 2006/023231, "International Preliminary Report on Patentability Chapter I (IB/373)", dated Jan. 30, 2007, 5 pages.

WO 2006/023231, "Written Opinion of the International Search Authority", dated Jan. 27, 2007, 4 pages.

\* cited by examiner

FLUORESCENT METAL ION INDICATORS WITH LARGE STOKES SHIFTS

CROSS-REFERENCE TO RELATED APPLICATIONS

This application is a divisional of U.S. Ser. No. 14/307,445, filed Jun. 17, 2014, which is a continuation of U.S. Ser. No. 13/194,727, filed Jul. 29, 2011, now U.S. Pat. No. 8,785,208, which is a continuation of U.S. Ser. No. 12/651,138, filed Dec. 31, 2009, now abandoned, which is a continuation of U.S. Ser. No. 12/484,903, now abandoned, filed Jun. 15, 2009, which is a continuation of U.S. Ser. No. 12/180,273, now abandoned, filed Jul. 25, 2008, which is a continuation of U.S. Ser. No. 11/191,799, now abandoned, filed Jul. 27, 2005, which claims priority to U.S. Ser. No. 60/591,750, filed Jul. 27, 2004, which disclosures are herein incorporated by reference.

FIELD OF THE INVENTION

The present invention relates to novel compositions and methods for the detection and isolation of metal ions, including physiological concentrations of calcium. The invention has applications in the fields of cell biology, neurology, immunology and proteomics.

BACKGROUND OF THE INVENTION

Metal ions play an important role in biological systems. Cells utilize metal ions for a wide variety of functions, such as regulating enzyme activity, protein structure, cellular signaling, as catalysts, as templates for polymer formation and as regulatory elements for gene transcription. Metal ions can also have a deleterious effect when present in excess of bodily requirements or capacity to excrete. A large number of natural and synthetic materials are known to selectively or non-selectively bind to or chelate metal ions. Ion chelators are commonly used in solution for in vivo control of ionic concentrations and detoxification of excess metals, and as in vitro buffers. When bound to a fluorophore, ion chelators are typically used as optical indicators of ions and are useful in the analysis of cellular microenvironments or dynamic properties of proteins, membranes and nucleic acids.

Such indicators are also useful for measuring ions in extracellular spaces; in vesicles; in vascular tissue of plants and animals; biological fluids such as blood and urine; in fermentation media; in environmental samples such as water, soil, waste water and seawater; and in chemical reactors.

Optical indicators for ions are important for qualitative and quantitative determination of ions, particularly in living cells. Fluorescent indicators for metal cations also permit the continuous or intermittent optical determination of these ions in living cells, and in solutions containing the ions.

A variety of fluorescent indicators that are useful for the detection of biologically relevant soluble free metal ions (such as $Ca^{2+}$, $Mg^+$ and $Zn^{2+}$) have been described that utilize oxygen-containing anionic or polyanionic chelators to bind to metal ions. In particular, fluorescent indicators utilizing a polycarboxylate BAPTA chelator have been previously described (U.S. Pat. No. 4,603,209 to Tsien et al. (1986); U.S. Pat. No. 5,049,673 to Tsien et al. (1991); U.S. Pat. No. 4,849,362 to DeMarinis et al. (1989); U.S. Pat. No. 5,453,517 to Kuhn et al. (1995); U.S. Pat. No. 5,501,980 to Malekzadeh et al. (1996); U.S. Pat. No. 5,459,276 to Kuhn et al. (1995); U.S. Pat. No. 5,501,980 to Katerinopoulos et al. (1996); U.S. Pat. No. 5,459,276 to Kuhn et al. (1995).

In general, a useful property for metal ion indicators is the ability to detect and/or quantify a selected metal ion in the presence of other metal ions. Discrimination of $Ca^{2+}$, $Na^+$ and $K^+$ ions in the presence of other metal ions is particularly useful for certain biological or environmental samples. For most biological applications, it is essential that the indicators be effective in aqueous solutions. It is also useful that indicators for biological applications be relatively insensitive to pH changes over the physiological range (pH 6-8) and sensitive to ion concentrations in the physiological range (for calcium, a $K_d$ of about 100 μM to about 100 nM). It is also beneficial if the indicator absorbs and emits light in the visible spectrum where biological materials have low intrinsic absorbance or fluorescence.

Also useful are chelators that possess a chemically reactive functional group, so that the chelating group can be attached to polymers for use in remote sensing of ions or enhancing the solubility or localization of the optical sensor. Many chelators bind to intracellular proteins, altering the chelator's metal binding properties. In addition, due to their relatively small size, they are readily sequestered non-selectively in intracellular vesicles, further limiting their effectiveness. One means of circumventing these problems is to attach the chelate compound to a large, water-soluble polysaccharide, such as dextran or FICOL, by means of modification of the polysaccharide to allow covalent attachment of the indicator. Dextrans and FICOLs are especially suitable for this application, as they are low cost, optically transparent above about 250 nm and available in multiple ranges of molecular weights. Furthermore, polysaccharides and their conjugates are reasonably compatible with most biological materials and do not interact significantly with intracellular components. Although fluorescent polysaccharides have been previously described, as have indicator conjugates of dextrans, none possess the advantageous properties of the indicator conjugates of the current invention.

The chelators of the invention show significant ability to discriminate between metal ions under physiological conditions, particularly $Ca^{2+}$, $Na^+$ and $K^+$ ions. This selectivity can be tailored by careful selection of chelate substituents. The compounds of the invention are typically soluble in aqueous solutions.

The compounds of the invention that act as indicators for target ions absorb and emit light in the visible spectrum and possess significant utility as a means of detecting and quantifying certain metal ion levels in living cells, biological fluids or aqueous solutions. Upon binding the target ion in the chelating moiety of the indicator, the optical properties of the attached fluorophore are generally affected in a detectable way by photoinduced electron transfer (PET), and this change is correlated with the presence of the ion according to a defined standard. Compounds having relatively long wavelength excitation and emission bands can be used with a variety of optical devices and require no specialized (quartz) optics, such as are required by indicators that are excited or that emit at shorter wavelengths. These indicators are suitable for use in fluorescence microscopy, flow cytometry, fluoroscopy, or any other application that currently utilize fluorescent metal ion indicators.

The distinguishing feature of the present compounds is the alkylene spacer between the chelating moiety and the reporter moiety, thus limiting the interaction between the ion sensor and reporter to the PET mechanism. Although several metal sensors based on PET are known in the art (U.S. Pat. Nos. 6,124,135; 6,359,135; He et al. Chem. Soc. (2003)

125:1468-1469; He et al. Anal. Chem (2003) 75:3549-55), they are limited to the non-charged crown ether or cryptand moieties, which are unable to interact with calcium ions, an important physiological metal ion. Also the reported PET sensors employ a different linkage (formed by alkylation reaction, rather than acylation utilized in this invention) between the functional elements. The present compounds provide a high affinity for calcium ions and a larger Stokes shift compared to other BAPTA-based calcium indicators (U.S. Pat. No. 5,049,673). The present invention provides an improvement over known calcium indicators, which has many important implications including the use in multicolor fluorescent assays.

SUMMARY OF THE INVENTION

The present invention provides a novel class of fluorogenic metal ion indicators that produce a detectable signal that is modulated by photoinduced electron transfer (PET), compositions, methods of use and kits for detecting metal ions in a sample. The metal ions bound and detected by the present compounds include, but are not limited to, $Ca^{2+}$, $Zn^{2+}$, $Mg^{2+}$, $Ga^{3+}$, $Tb^{3+}$, $La^{3+}$, $Pb^{2+}$, $Hg^{2+}$, $Cd^{2+}$, $Cu^{2+}$, $Ni^{2+}$, $Co^{2+}$, $Fe^{2+}$, $Mn^{2+}$, $Ba^{2+}$, and $Sr^{2+}$. Particularly relevant in biological systems are the metal ions selected from the group consisting of $Ca^{2+}$, $Mg^{2+}$, $Fe^{2+}$ and $Zn^{2+}$.

The present compounds exhibit a Stokes shift great than about 50 nm, preferably greater than about 100 nm, more preferably greater than 150 nm and most preferably greater than 200 nm when bound by a metal ion capable of being chelated by the chelating moiety and illuminated with an appropriate wavelength. In certain aspects, the present compounds exhibit a Stokes shift greater than about 250 nm.

In an exemplary embodiment, a present compound for the detection of metal ions wherein a detectable response is a result of photoinduced electron transfer (PET), comprise a metal chelating moiety and a fluorophore or a fluorescent protein (reporter moiety) that is covalently bonded to the metal chelating moiety by linker —$(CR_2)_n$NR'— or —$(CR_2)_n$— wherein R and R' are independently selected from the group consisting of hydrogen, alkyl, and substituted alkyl and n is 1-10. When the linker is —$(CR_2)_n$— a terminal carbon must be directly and covalently bonded to a nitrogen atom of the fluorophore. In a further embodiment the present compound is utilized to bind and detect calcium ions wherein a detectable response is a result of photoinduced electron transfer (PET), wherein the compound comprises a metal chelating moiety that is capable of binding calcium ions and a fluorophore that is covalently bonded to the metal chelating moiety by a linker —$(CR_2)_n$NR'— or —$(CR_2)_n$— wherein R and R' are independently selected from the group consisting of hydrogen, alkyl, and substituted alkyl and n is 1-10. Again, if the linker is —$(CR_2)_n$— a terminal carbon of the linker must be bound to a nitrogen atom of the fluorophore.

Many chelating moieties are known that bind metal ions and find use in detecting metal ions in biological systems. BAPTA is one such chelating moiety that is well known for its ability to bind and detect calcium ions when conjugated to a reporter molecule. Thus, the use of the BAPTA moiety in conjunction with the present linkers and reporter moiety provides a novel compound that represents an improvement over known calcium indicators. These present calcium indicators demonstrate improved affinity for calcium ions and a larger Stokes shift in comparison to other BAPTA-based calcium indicators such as the indicator sold under the trade name Fluo-3 (Molecular Probes, Inc.)

A present compound based on the BAPTA chelator has the formula:

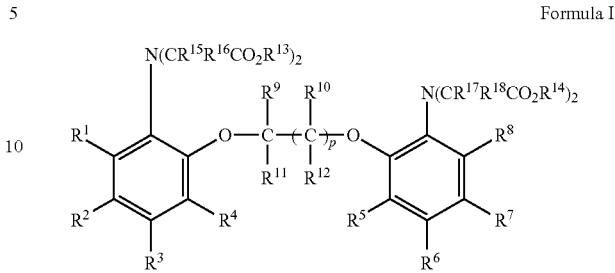

Formula I wherein $R^{15}$, $R^{16}$, $R^{17}$ and $R^{18}$ are independently H or $C_1$-$C_6$ alkyl; and $R^{13}$ and $R^{14}$ are independently hydrogen, $C_1$-$C_6$ alkyl, —$CH_2OCOCH_3$ or a salt ion;

$R^1$-$R^8$ are selected independently from the group consisting of hydrogen, halogen, $C_1$ to $C_{10}$ alkyl ($CH_2$), methoxy (—$OCH_3$), hydroxyl (—OH), $C_2$-$C_6$ alkoxy (—$OCH_2$), alicyclic, heteroalicyclic, aryl, heteroaryl, amino (—$NR^{19}R^{20}$), aldehyde, carboxyl, azido, nitro, nitroso, cyano, thioether, sulfonyl, reactive group, carrier molecule, solid support, reporter molecule, —$(CR_2)_n$NR'R", —$(CR_2)_n$NR'-fluorophore and —$(CR_2)_n$-fluorophore or a member selected from $R^1$ in combination with $R^2$; $R^2$ in combination with $R^3$; $R^3$ in combination with $R^4$; $R^5$ in combination with $R^6$; $R^6$ in combination with $R^7$; and $R^7$ in combination with $R^8$ together with the atoms to which they are joined, form a ring which is a 5-, 6- or 7-membered cycloalkyl, a substituted 5-, 6- or 7-membered cycloalkyl, a 5-, 6- or 7-membered heterocycloalkyl, a substituted 5-, 6- or 7-membered heterocycloalkyl, a 5-, 6- or 7-membered aryl, a substituted 5-, 6- or 7-membered aryl, a 5-, 6- or 7-membered heteroaryl, or a substituted 5-, 6- or 7-membered heteroaryl;

wherein R, and R' are independently selected from the group consisting of hydrogen, alkyl, and substituted alkyl;

R" is independently selected from the group consisting of hydrogen, alkyl, substituted alkyl, fluorophore, carrier molecule, solid support and reactive group; and n is 1-10; and, wherein $R^{19}$ and $R^{20}$ are independently selected from the group consisting of H, $C_1$-$C_6$ alkyl, substituted alkyl, $C_1$-$C_6$ carboxyalkyl (—$(CH_2)_{1-6}COOR^{13}$), an alpha-acyloxyalkyl, a biologically compatible salt, aryl, substituted aryl, aryl alkyl, substituted aryl alkyl, heteroaryl, and substituted heteroaryl;

$R^9$, $R^{10}$, $R^{11}$ and $R^{12}$, are independently selected from the group consisting of hydrogen, a reactive group, a carrier molecule, a solid support, —$(CR_2)_n$NR'R", —$(CR_2)_n$NR'-fluorophore and $C_1$-$C_6$ alkyl, or a member selected from $R^9$ in combination with $R^{10}$; or $R^{11}$ in combination with $R^{12}$ together with the atoms to which they are joined, form a ring which is a 5-, or 6-membered alicyclic ring, a substituted 5-, or 6-membered alicyclic ring, a 5-, or 6-membered heterocyclic ring, or a substituted 5-, or 6-membered heterocyclic ring;

p is 0, 1, 2 or 3;

wherein at least one of $R^1$-$R^{12}$ is —$(CR_2)_n$NR'R", —$(CR_2)_n$NR'-fluorophore or —$(CR_2)_n$-fluorophore with the proviso that when at least one of the $R^1$-$R^{12}$ is —$(CR_2)_n$-fluorophore that the fluorophore comprise a nitrogen atom that is covalently bonded to the —$(CR_2)_n$—.

In one aspect exactly one of $R^1$-$R^8$ is —$(CR_2)_n$NR'-fluorophore or —$(CR_2)_n$-fluorophore, in a further aspect, exactly one of $R^2$, $R^3$, $R^6$ or $R^7$ is —$(CR_2)_n$NR'-fluorophore or —(CR$_2$)$_n$-fluorophore. In one embodiment R and R' are each hydrogen. The fluorophore can be any reporter moiety known to one of skill in the art. Such a fluorophore includes, but are not limited to, those fluorophores selected from the group consisting of dansyl, xanthene, cyanine, borapolyazaindacene, pyrene, naphthalene, coumarin, oxazine and derivatives thereof. The xanthenes are further classified to include the members selected from the group consisting of fluorescein or derivatives thereof, rhodamine or derivatives thereof, rhodol or derivatives thereof, and rosamine or derivatives thereof. In a particular embodiment, the fluorophore is a xanthene, particularly fluorescein or a derivative thereof, and the linker is —(CH$_2$)$_n$NR'—. In another particular embodiment, the fluorophore is dansyl and the linker is —(CH$_2$)$_n$NR'—. In an alternative embodiment the linker is —(CH$_2$)$_n$— wherein the fluorophore is naphthalene. Exemplary compounds include members selected from the group consisting of Compound 5, 6, 9, 10, 13, 14 and 15.

The present fluorophores are independently substituted by substituents selected from the group consisting of hydrogen, halogen, amino, substituted amino, alkyl, substituted alkyl, aryl, substituted aryl, heteroaryl, substituted heteroaryl, alkoxy, sulfo, and reactive group. In one aspect, a xanthene fluorophore is substituted by halogen such as fluorine, chlorine or bromine.

In an exemplary embodiment, the nitrogen substitutents $R^{15}$, $R^{16}$, $R^{17}$ and $R^{18}$ are each hydrogen. In a further embodiment, $R^{13}$ and $R^{14}$ are independently hydrogen or a salt ion representing a cell impermeant version of the present metal ion indicators. In yet another embodiment $R^{13}$ and $R^{14}$ are independently —CH$_2$OCOCH$_3$ represent a cell permeant version of the present compounds. Alternatively, $R^{13}$ and $R^{14}$ are each CH$_3$, also representing a cell permeant version of the present compounds.

The reactive group, solid support and carrier molecule when substituted on the present compounds comprise a linker that is a single covalent bond, or a covalent linkage that is linear or branched, cyclic or heterocyclic, saturated or unsaturated, having 1-20 nonhydrogen atoms selected from the group consisting of C, N, P, O and S; and are composed of any combination of ether, thioether, amine, ester, carboxamide, sulfonamide, hydrazide bonds and aromatic or heteroaromatic bonds.

The reactive group is selected from the group consisting of an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a reactive platinum complex, a silyl halide, a sulfonyl halide, a thiol and a photoactivatable group. In a particular embodiment the reactive group is selected from the group consisting of carboxylic acid, succinimidyl ester of a carboxylic acid, hydrazide, amine and a maleimide.

The carrier molecule is selected from the group consisting of an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell or a virus. In a particular embodiment the carrier molecule is selected from the group consisting of an antibody or fragment thereof, an avidin or streptavidin, a biotin, a blood component protein, a dextran, an enzyme, an enzyme inhibitor, a hormone, an IgG binding protein, a fluorescent protein, a growth factor, a lectin, a lipopolysaccharide, a microorganism, a metal binding protein, a metal chelating moiety, a non-biological microparticle, a peptide toxin, a phosphotidylserine-binding protein, a structural protein, a small-molecule drug, or a tyramide.

The solid support is selected from the group consisting of a microfluidic chip, a silicon chip, a microscope slide, a microplate well, silica gels, polymeric membranes, particles, derivatized plastic films, glass beads, cotton, plastic beads, alumina gels, polysaccharides, polyvinylchloride, polypropylene, polyethylene, nylon, latex bead, magnetic bead, paramagnetic bead, and superparamagnetic bead. In a particular embodiment the solid support is selected from the group consisting of Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose and starch.

In a further embodiment of the present invention, the present compounds form a composition with a metal ion wherein the composition comprises any present compound and a metal ion that is capable of being chelated by the compound.

The present compounds can be utilized to bind, detect, quantitate, monitor and further analyze metal ions. Thus, an exemplary method for binding a target metal ion in a sample, comprising steps of:
  a. contacting the sample with a present compound to form a contacted sample; and,
  b. incubating the contacted sample for a sufficient amount of time to allow the compound to chelate the target metal ion whereby the metal ion is bound.

The metal ions that can be bound by the present compounds include, but are not limited to, $Ca^{2+}$, $Zn^{2+}$, $Mg^{2+}$, $Ga^{3+}$, $Tb^{3+}$, $La^{3+}$, $Pb^{2+}$, $Hg^{2+}$, $Cd^{2+}$, $Cu^{2+}$, $Ni^{2+}$, $Co^{2+}$, $Fe^{2+}$, $Mn^{2+}$, $Ba^{2+}$, and $Sr^{2+}$. Particularly relevant are those metal ions that are present in biological systems such as those selected from the group consisting of $Ca^{2+}$, $Mg^{2+}$, $Fe^{2+}$ and $Zn^{2+}$. In an exemplary embodiment, the present compounds are used to bind calcium ions.

The sample typically is or comprises a biological system wherein the sample is selected from the group consisting of live cells, intracellular fluids, extracellular fluids, biological fluids, biological fermentation media, environmental sample, industrial samples, proteins, peptides, buffer solutions or biological fluids and chemical reactors. In a further embodiment the sample is selected from the group consisting of blood cells, immune cells, cultured cells, muscle tissue, neurons, extracellular vesicles; vascular tissue, blood fluids, saliva, urine; water, soil, waste water, sea water; pharmaceuticals, foodstuffs and beverages.

The present method further comprises detecting a target metal ion wherein the sample is illuminated with an appropriate wavelength whereby the target metal ion is detected. In this instance the present compounds comprise a reporter moiety, typically a fluorophore.

In an exemplary embodiment the present compounds are utilized to detect metal ions in a live cell wherein the compounds comprise a lipophilic group such as an AM or acetate ester. In this instance the method for detecting target ions in a live cell comprises the steps of:
  a) contacting a sample of live cells with a present compound with the proviso that at least one of $R^{13}$ or $R^{14}$ is —CH$_2$OCOCH$_3$ or CH$_3$;
  b) incubating the sample and the compound for sufficient time to allow the compound to chelate the target metal ion; and, c) illuminating the sample with an appropriate wavelength to generate a detectable signal that is a result of PET whereby the target ion is detected in a live cell.

In this instance the metal ion to be detected includes those members selected from the group consisting of $Hg^{2+}$, $Ni^{2+}$, $Ca^{2+}$, $Mg^{2+}$, $Fe^{2+}$ and $Zn^{2+}$.

The present invention also provides kits for binding, detecting, quantitating, monitoring and otherwise analyzing metal ions wherein the kit comprises at least one compound according to the present invention and instructions for use thereof. In a further embodiment, the kit comprises one or more components selected from the group consisting of a calibration standard of a metal ion, an ionophore, a metal ion indicator other than for calcium ions, a detectable signal standard, an aqueous buffer solution, an antibody or fragment thereof, a reference dye standard and an organic solvent.

DETAILED DESCRIPTION OF THE INVENTION

Introduction

Figure 1:
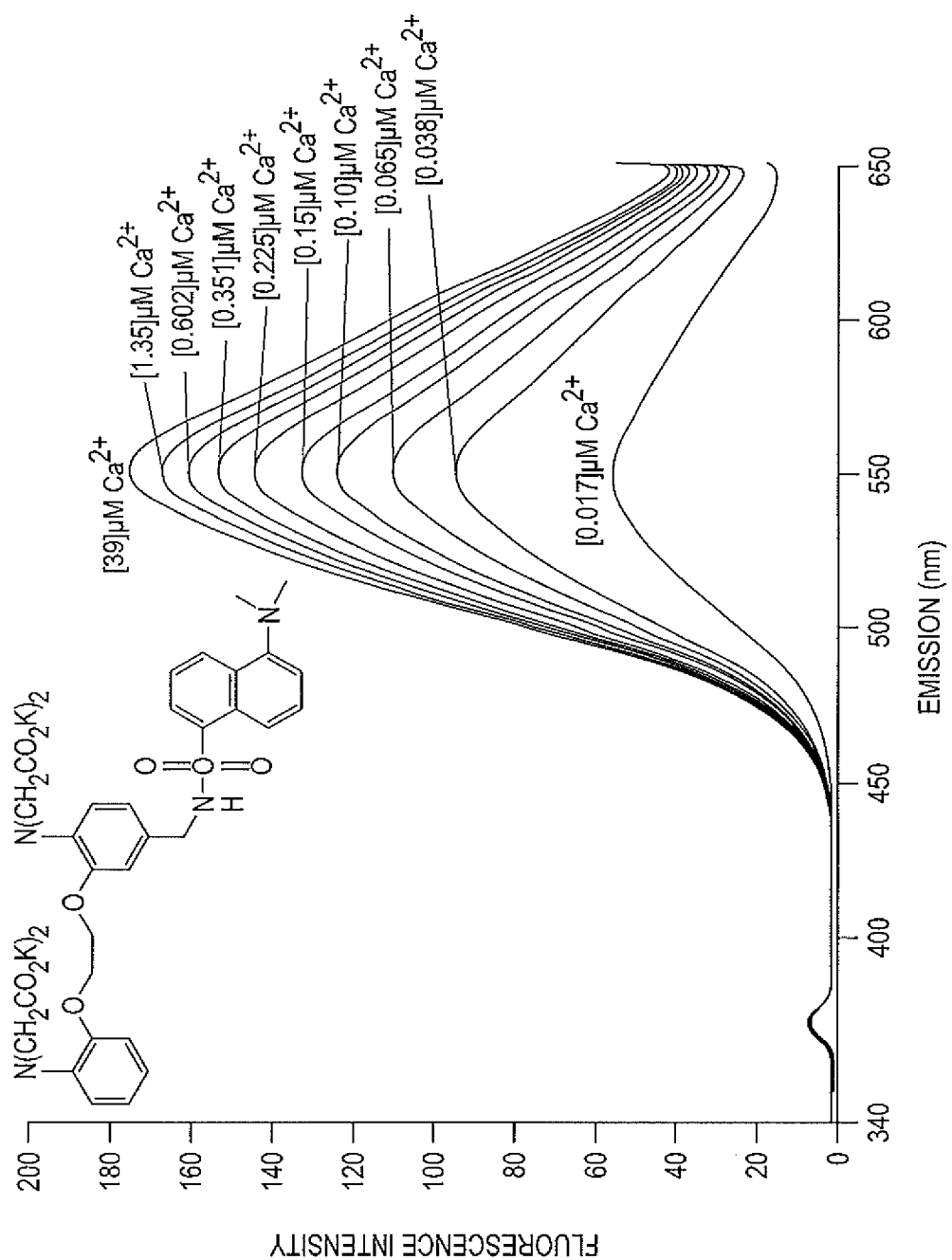
FIG. 1: Shows the binding and detection of a titration (0 μM to 39 μM) of calcium ions in solution wherein a Stokes shift of about 220 nm was observed. The calcium ion solution containing the present compound was excited at a wavelength of 331 nm and the resulting emission wavelength was at 549 nm.
Figure 2:
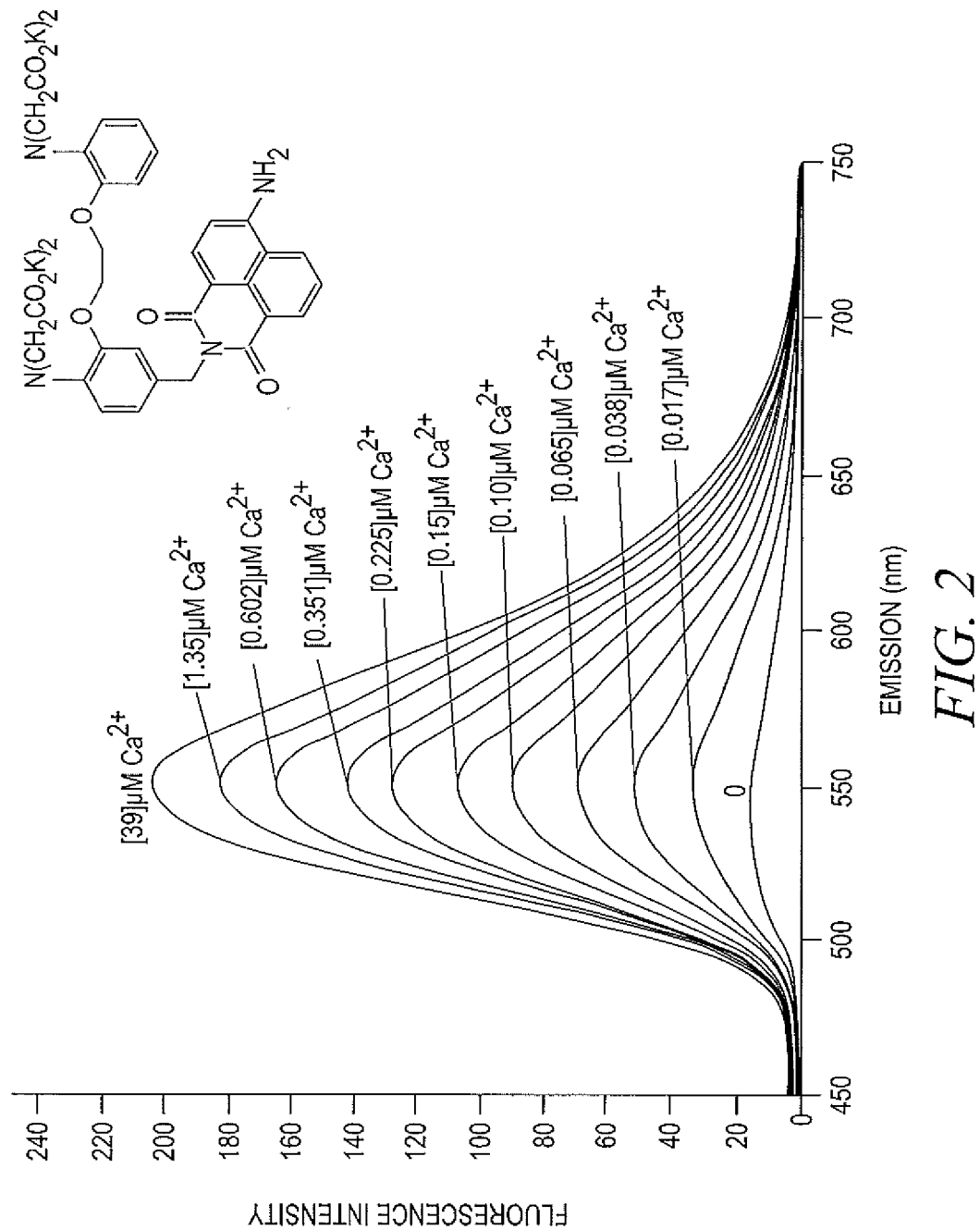
FIG. 2: Shows the binding and detection of a titration (0 μM to 39 μM) of calcium ions in solution wherein a Stokes shift of about 120 nm was observed. The calcium ion solution containing the present compound was excited at a wavelength of 432 nm and the resulting emission wavelength was at 550 nm.
Figure 3:
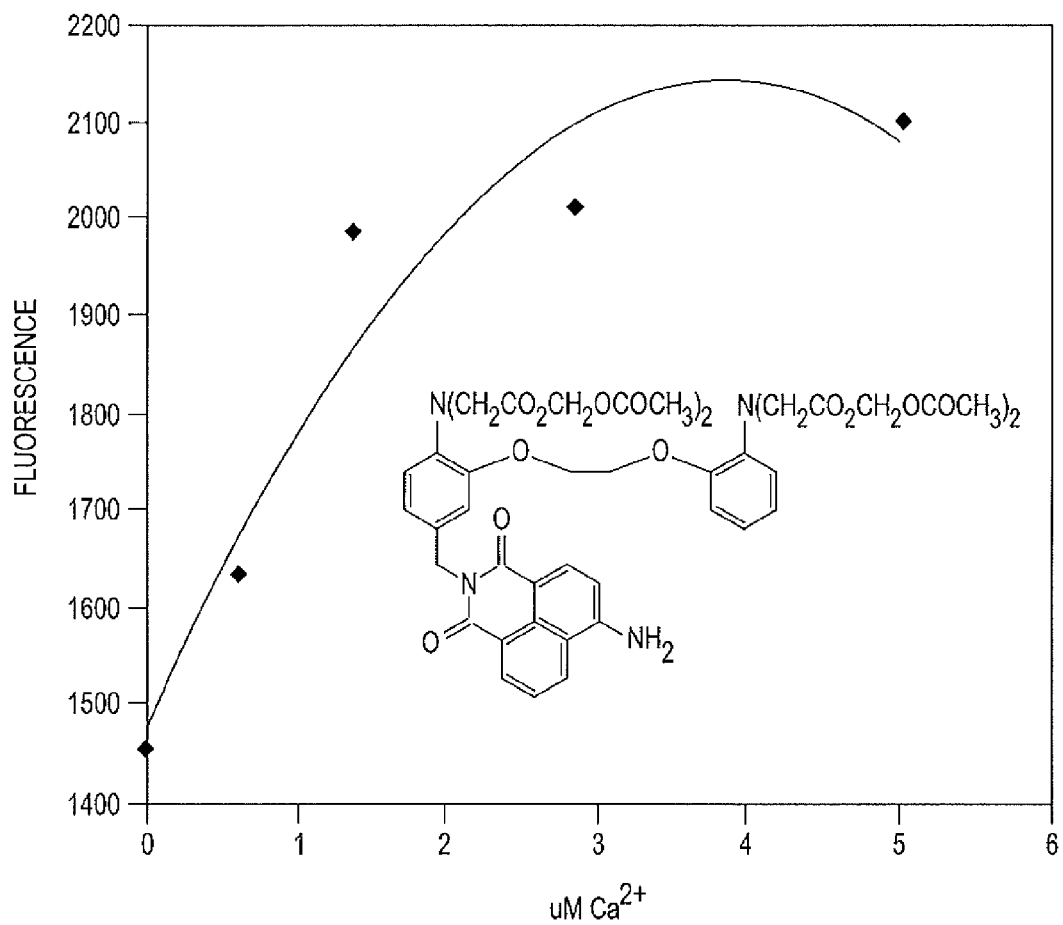
FIG. 3: Shows the detection of intracellular calcium ions in live Jurkat cells using a live cell version of the present compound.

The present invention is based upon the phenomenon in which the optical properties of a fluorophore can be modulated by strategic covalent attachment of a metal ion-binding moiety (a chelator). In the invention, it has been found that certain ion chelators reduce the fluorescence of the fluorophore by a through-space interaction known as PET, in which fluorescence is inhibited by interaction of the excited state fluorophore with an electron-rich chelator moiety. As the chelator moiety binds metal ion(s), the PET effect is diminished, resulting in increased fluorescence from the fluorophore.

Definitions

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a metal chelator" includes a plurality of chelators and reference to "a metal ion" includes a plurality of ions and the like.

Unless defined otherwise, all technical and scientific terms used herein have the same meaning as commonly understood by one of ordinary skill in the art to which this invention is related. The following terms are defined for purposes of the invention as described herein.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose an appropriate method for a particular situation. See, generally, Furniss et al. (eds.), VOGEL'S ENCYCLOPEDIA OF PRACTICAL ORGANIC CHEMISTRY 5$^{TH}$ ED., Longman Scientific and Technical Ltd., Essex, 1991, pp. 809-816; and Heller, *Acc. Chem. Res.* 23: 128 (1990).

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —$CH_2O$— is intended to also recite —$OCH_2$—.

The term "acyl" or "alkanoyl" by itself or in combination with another term, means, unless otherwise stated, a stable straight or branched chain, or cyclic hydrocarbon radical, or combinations thereof, consisting of the stated number of carbon atoms and an acyl radical on at least one terminus of the alkane radical. The "acyl radical" is the group derived from a carboxylic acid by removing the —OH moiety therefrom.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

Exemplary alkyl groups of use in the present invention contain between about one and about twenty five carbon atoms (e.g. methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a straight or branched chain, or cyclic carbon-containing radical, or combinations thereof, consisting of the stated number of carbon atoms and at least one heteroatom selected from the group consisting of O, N, Si, P and S, and wherein the nitrogen, phosphorous and sulfur atoms are optionally oxidized, and the nitrogen heteroatom is optionally quaternized. The heteroatom(s) O, N, P, S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1 (1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R"

is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O) $CF_3$, —C(O)$CH_2OCH_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R"', —OC(O)R', —C(O)R', —$CO_2$R', —CONR'R", —OC(O) NR'R", —NR"C(O)R', —NR'—C(O)NR"R"', —NR"C(O)$_2$ R', —NR—C(NR'R"R"')=NR"", —NR—C(NR'R") =NR"', —S(O)R', —S(O)$_2$R', —S(O)$_2$NR'R", —NRSO$_2$R', —CN and NO$_2$, —R', —N$_3$, —CH(Ph)$_2$, fluoro($C_1$-$C_4$) alkoxy, and fluoro($C_1$-$C_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present. In the schemes that follow, the symbol X represents "R" as described above.

Two of the substituents on adjacent atoms of the aryl or heteroaryl ring may optionally be replaced with a substituent of the formula T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R"')$_d$—, where s and d are independently integers of from 0 to 3, and X is —O—, —NR'—, —S—, —S(O)—, —S(O)$_2$—, or —S(O)$_2$NR'—. The substituents R, R', R" and R"' are preferably independently selected from hydrogen or substituted or unsubstituted ($C_1$-$C_6$)alkyl.

As used herein, the term "heteroatom" includes oxygen (O), nitrogen (N), sulfur (S), phosphorus (P) and silicon (Si).

The term "amino" or "amine group" refers to the group —NR'R" (or N±FIR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —N±FIR'R" and its biologically compatible anionic counterions.

The term "affinity" as used herein refers to the strength of the binding interaction of two molecules, such as a metal chelating compound and a metal ion or a positively charged moiety and a negatively charged moiety.

The term "aqueous solution" as used herein refers to a solution that is predominantly water and retains the solution characteristics of water. Where the aqueous solution contains solvents in addition to water, water is typically the predominant solvent.

The term "carrier molecule" as used herein refers to a compound of the present invention that is covalently bonded to a biological or a non-biological component. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof.

The term "cell permeable" as used herein refers to compounds of the present invention that are able to cross the cell membrane of live cells. Lipophilic groups that are covalently attached to the present compounds, facilitate this permeability and live cell entry. Once inside the cells, the lipophilic groups are hydrolyzed resulting in charged molecules that are well retained in living cells. Particularly useful lipophilic groups include acetoxymethyl (AM) ester and acetate esters wherein once inside the cells the groups are cleaved by nonspecific esterases resulting in charged molecules.

The term "complex" as used herein refers to the association of two or more molecules, usually by non-covalent bonding.

The term "detectable response" as used herein refers to a change in or an occurrence of, a signal that is directly or indirectly detectable either by observation or by instrumentation and the presence or magnitude of which is a function of the presence of a target metal ion in the test sample. Typically, the detectable response is an optical response resulting in a change in the wavelength distribution patterns or intensity of absorbance or fluorescence or a change in light scatter, fluorescence quantum yield, fluorescence lifetime, fluorescence polarization, a shift in excitation or emission wavelength or a combination of the above parameters. The detectable change in a given spectral property is generally an increase or a decrease. However, spectral changes that result in an enhancement of fluorescence intensity and/or a shift in the wavelength of fluorescence emission or excitation are also useful. The change in fluorescence on ion binding is usually due to conformational or electronic changes in the indicator that may occur in either the excited or ground state of the fluorophore, due to changes in electron density at the ion binding site, due to quenching of fluorescence by the bound target metal ion, or due to any combination of these or other effects. Alternatively, the detectable response is an occurrence of a signal wherein the fluorophore is inherently fluorescent and does not produce a change in signal upon binding to a metal ion or biological compound.

The term "fluorophore" as used herein refers to a composition that is inherently fluorescent or demonstrates a change in fluorescence upon binding to a biological compound or metal ion, or metabolism by an enzyme, i.e., fluorogenic. Fluorophores may be substituted to alter the solubility, spectral properties or physical properties of the fluorophore. Numerous fluorophores are known to those skilled in the art and include, but are not limited to coumarin, acridine, furan, dansyl, cyanine, pyrene, naphthalene, benzofurans, quinolines, quinazolinones, indoles, benzazoles, borapolyazaindacenes, oxazine and xanthenes, with the latter including fluoresceins, rhodamines, rosamine and rhodols as well as other fluorophores described in RICHARD P. HAUGLAND, MOLECULAR PROBES HANDBOOK OF FLUORESCENT PROBES AND RESEARCH CHEMICALS (9$^{th}$ edition, including the CD-ROM, September 2002). The fluorophore moiety may be substituted by substituents that enhance solubility, live cell permeability and alter spectra absorption and emission.

The term "kit" as used refers to a packaged set of related components, typically one or more compounds or compositions.

The term "metal chelator" or "metal chelating compound" as used herein refers to a chemical compound that combines with a metal ion to form a chelate ring structure.

The term "metal ion" or "target metal ion" as used herein refers to any metal cation that is capable of being chelated by the present BAPTA metal chelating compound. Typically, these metal ions are physiological and or nutritional relevant metal ion such as $Na^+$, $K_+$, $Zn^{2+}$, $Mg^{2+}$, $Fe^{2+}$, and $Ca^{2+}$. The term metal ion used herein also refers to the metal ions $Ga^{3+}$, $Tb^{3+}$, $La^{3+}$, $Pb^{2+}$, $Hg^{2+}$, $Cd^{2+}$, $Cu^{2+}$, $Ni^{2+}$, $Co^{2+}$, $Mn^{2+}$, $Ba^{2+}$, and $Sr^{2+}$.

The term "photoinduced electron transfer (PET)" as used herein refers to intramolecular electron transfer.

The terms "protein" and "polypeptide" are used herein in a generic sense to include polymers of amino acid residues of any length. The term "peptide" as used herein refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. In addition, other peptidomimetics are also useful in the present invention. For a general review, see, Spatola, A. F., in *Chemistry and Biochemistry of Amino Acids, Peptides and Proteins*, B. Weinstein, eds., Marcel Dekker, New York, p. 267 (1983).

The term "reactive group" as used herein refers to a group that is capable of reacting with another chemical group to form a covalent bond, i.e. is covalently reactive under suitable reaction conditions, and generally represents a point of attachment for another substance. The reactive group is a moiety, such as carboxylic acid or succinimidyl ester, on the compounds of the present invention that is capable of chemically reacting with a functional group on a different compound to form a covalent linkage. Reactive groups generally include nucleophiles, electrophiles and photoactivatable groups.

Exemplary reactive groups include, but are not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

The term "sample" as used herein refers to any material that may contain target metal ions, as defined above. Typically, the sample is a live cell or a biological fluid that comprises endogenous host cell proteins. Alternatively, the sample may be a buffer solution or an environmental sample containing target metal ions. The sample may be in an aqueous solution, a viable cell culture or immobilized on a solid or semi solid surface such as a polyacrylamide gel, membrane blot or on a microarray.

The term "Stokes shift" as used herein refers to the difference in wavelength between absorbed and emitted energy. Specifically, the Stokes shift is the difference (usually in frequency units) between the spectral positions and the band maxima (or band origin) of the absorption and luminescence arising from the same electronic transitions.

The Compounds

In general, for ease of understanding the present invention, the metal ion binding compounds and corresponding substituents will first be described in detail, followed by the many and varied methods in which the compounds find uses, which is followed by exemplified methods of use and synthesis of certain novel compounds that are particularly advantageous for use with the methods of the present invention.

The present compounds find utility in binding target metal ions in a sample. The sample includes live cells or a biological fluid that comprises endogenous host cell proteins, buffer solutions and environmental samples. Therefore, the present compounds, when comprising a fluorophore or fluorescent protein moiety (reporter moiety), find utility in binding, isolating, quantitating, monitoring and detecting target metal ions wherein the detectable signal is modulated by photoinduced electron transfer (PET). Detection of target metal ions can also be accomplished in live cells wherein the present compound comprises a lipophilic group such as an AM or acetate ester that allows for entry across the live cell membrane. Once inside the cells nonspecific esterases cleave the AM or acetate ester resulting in a charged molecule that is well retained in the cell. These present compounds are particularly useful for binding physiologically relevant levels of calcium.

The present compounds consist of three functional elements, the ion sensing moiety (chelating moiety), the reporter moiety (fluorophore or fluorescent protein) and spacer or linker between the sensing and reporter moieties of the present compound that provides for photoinduced electron transfer (PET) upon binding of a metal ion and excitation by an appropriate wavelength. The distinguishing feature of these compounds is this linker, —$(CR_2)_n NR'$—, wherein the alkyl spacer prevents direct through-bond conjugation between the electron orbitals of the metal chelator and the reporter moiety. In this instance, as used herein "conjugation" refers to the sharing of pi-electrons between alternating pi orbitals. Thus, the metal chelator and reporter moiety are not conjugated, whereas other known chelators are conjugated to the reporter moiety resulting in a detectable signal that is not modulated by PET. This disruption of direct conjugation results in non-fluorescent compounds until a metal ion is bound by an appropriate metal ion and the compound is illuminated by an appropriate wavelength.

Alternatively, the linker is —$(CR_2)_n$— wherein the reporter moiety comprises a nitrogen atom that is covalently bonded to a carbon atom of the linker.

Therefore, the present compounds for the detection of metal ions wherein a detectable response is a result of photoinduced electron transfer (PET), and the compound comprises a metal chelating moiety and a fluorophore or a fluorescent protein that is covalently bonded to the metal chelating moiety by linker —$(CR_2)_n$NR'— or —$(CR_2)_n$— wherein R and R' are independently selected from the group consisting of hydrogen, alkyl, and substituted alkyl and n is 1-10. However, when the linker is —$(CR_2)_n$— the terminal carbon atom must be directly and covalently bonded to a nitrogen atom of the fluorophore.

In a more specific embodiment, the present compound binds and detects calcium ions wherein a detectable response is a result of photoinduced electron transfer (PET) and the compound comprises a metal chelating moiety and a fluorophore or a fluorescent protein that is covalently bonded to the metal chelating moiety by linker —$(CR_2)_n$NR'— or —$(CR_2)_n$— wherein R and R' are independently selected from the group consisting of hydrogen, alkyl, and substituted alkyl and n is 1-10. Again, when the linker is —$(CR_2)_n$— the terminal carbon atom of the linker must be directly and covalently bonded to a nitrogen atom of the fluorophore.

In all cases the present compounds exhibit a Stokes shift that is greater than about 50 nm, more preferably greater than about 100 nm, even more preferably greater than about 150 nm. In some instances the present compounds exhibit a Stokes shift greater than about 200 nm and in particularly desirable embodiments, the present compounds exhibit a Stokes shift greater than about 250 nm. This larger Stokes shift is advantageous for distinguishing the detectable signal from autofluorescence of biological samples and for the application of multicolor assays allowing for the simultaneous detection of multiple analytes. To the best of our knowledge the present compounds represent the only metal ion sensing compounds with a Stokes shift greater than about 50 nm, which represents a major improvement over known and commonly used metal ion indicators. This is particular advantageous for the detection of intracellular calcium ion concentrations.

Chelating Moiety

The ion-sensing or chelating moiety of the present compound is any moiety that will bind or chelate metal ions. Typically this results in a change in the fluorescent signal. Metal ions of the present invention, include but are not limited to, $Ca^{2+}$, $Zn^{2+}$, $Mg^{2+}$, $Ga^{3+}$, $Tb^{3+}$, $La^{3+}$, $Pb^{2+}$, $Hg^{2+}$, $Cd^{2+}$, $Cu^{2+}$, $Ni^{2+}$, $Co^{2+}$, $Fe^{2+}$, $Mn^{2+}$, $Ba^{2+}$, and $Sr^{2+}$. In one aspect the metal ion is a physiological relevant ion selected from the group consisting of $Ca^{2+}$, $Mg^{2+}$, $Fe^{2+}$ and $Zn^{2+}$. In a further aspect the metal ion is $Ca^{2+}$, which is most notably chelated by the well-known BAPTA chelating moiety.

The term "BAPTA" as used herein refers to a metal-chelating compound that is 1,2-bis(2-aminophenoxy)ethane-N,N,N',N'-tetraacetic acid or its analogs, derivatives, ring-fused variants and conjugates, and all metallic and nonmetallic salts, partial salts and hydrates thereof, including any corresponding compounds disclosed in U.S. Pat. Nos. 4,603,209; 4,849,362; 5,049,673; 5,453,517; 5,459,276; 5,516,911; 5,501,980; 6,162,931 and 5,773,227. When used generically, "BAPTA" refers to two benzene rings that are joined by a $C_1$-$C_3$ hydrocarbon bridge terminated by oxygen atoms, including methylenedioxy (—$OCH_2O$—), ethylenedioxy (—$OCH_2CH_2O$—) or propylenedioxy (—$OCH_2CH_2CH_2O$—) bridging groups, where each benzene ring is optionally substituted by one or more substituents that adjust the metal ionbinding affinity, solubility, chemical reactivity, spectral properties or other physical properties of the compound. BAPTA derivatives additionally include compounds in which the benzene rings of the BAPTA structure are substituted by or fused to additional aromatic, or heteroaromatic rings.

Thus, in one aspect the chelating moiety of the present compounds is represented by the formula:

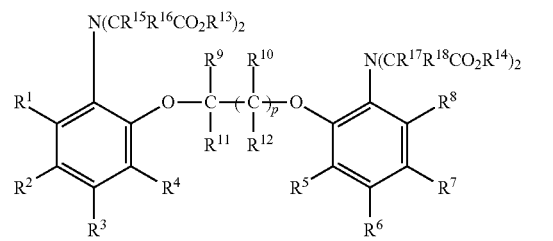

Formula I wherein $R^{15}$, $R^{16}$, $R^{17}$ and $R^{18}$ are independently hydrogen (H) or $C_1$-$C_6$ alkyl and $R^{13}$ and $R^{14}$ are independently hydrogen (H), $C_1$-$C_6$ alkyl, —$CH_2OCO$(alkyl) or a salt ion. In one aspect $R^{15}$, $R^{16}$, $R^{17}$ and $R^{18}$ are each hydrogen. When $R^{13}$ and $R^{14}$ are independently —$CH_2OCOCH_3$ or $CH_3$ the present compounds are utilized as live cell metal ion indicators. Alternatively, $R^{13}$ and $R^{14}$ are independently hydrogen or a salt ion wherein the resulting compounds are not capable of passively crossing the live cell membrane.

Thus, cell impermeant versions of the present compounds are, in one aspect, have the following formula:

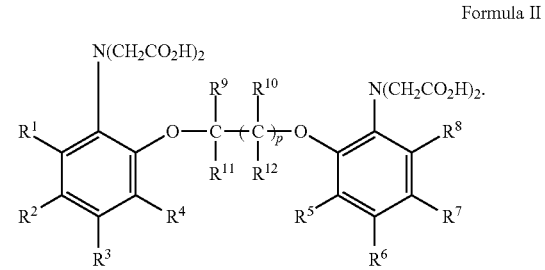

Formula II

The cell impermeant version of the compounds may be synthesized in this manner to be used for detection of metal ions in an environment other than live cells or the cell impermeant version may be a result of the cell permeant version that has been loaded in to live cells and subsequently cleaved by an intracellular enzyme. These cell permeant versions of the compounds are thus converted to cell impermeant version in the cells resulting in metal ion indicators that are well retained in live cells.

In one aspect, the live-cell versions of the present compounds have the following formula:

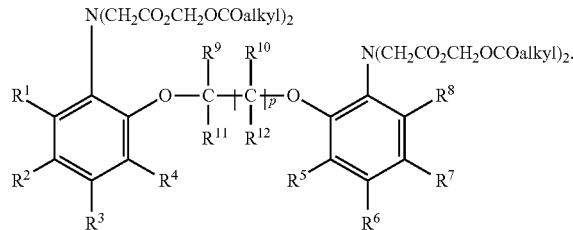

Formula III

Wherein the present compound comprises a substrate for a non-specific ester, typically the compound comprises an AM ester wherein R13 and/or R14 are —CH$_2$OCOCH$_3$.

In another aspect, the compounds are according to the following formula:

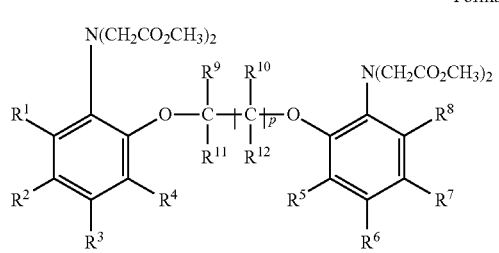

Formula IV wherein the compound comprises an acetate group.

The benzene substituents, $R^1$, $R^2$, $R^3$, $R^4$, $R^5$, $R^6$, $R^7$ and $R^8$ are typically substituted by substitutents well known in the art for BAPTA compounds. These substituents are selected independently from the group consisting of hydrogen, halogen, $C_1$ to $C_{10}$ alkyl (CH$_2$), methoxy (—OCH$_3$), hydroxyl (—OH), $C_2$-$C_6$ alkoxy (—OCH$_2$), alicyclic, heteroalicyclic, aryl, heteroaryl, amino (—NR$^{19}$R$^{20}$, aldehyde, carboxyl, azido, nitro, nitroso, cyano, thioether, sulfonyl, reactive group, carrier molecule, solid support, reporter molecule, —(CR$_2$)$_n$NR'R", —(CR$_2$)$_n$NR'-fluorophore and (CR$_2$)$_n$-fluorophore. Alternatively, any two adjacent ring substituents in combination constitute a cyclic substituent that is substituted or unsubstituted cycloalkyl, cycloheteroalkyl, aryl, fused aryl, heteroaryl or fused heteroaryl. In one aspect a member selected from $R^1$ in combination with $R^2$; $R^2$ in combination with $R^3$; $R^3$ in combination with $R^4$; $R^5$ in combination with $R^6$; $R^6$ in combination with $R^7$; and $R^7$ in combination with $R^8$ together with the atoms to which they are joined, form a ring which is a 5-, 6- or 7-membered cycloalkyl, a substituted 5-, 6- or 7-membered cycloalkyl, a 5-, 6- or 7-membered heterocycloalkyl, a substituted 5-, 6- or 7-membered heterocycloalkyl, a 5-, 6- or 7-membered aryl, a substituted 5-, 6- or 7-membered aryl, a 5-, 6- or 7-membered heteroaryl, or a substituted 5-, 6- or 7-membered heteroaryl.

The amino substituents, $R^{19}$ and $R^{20}$, are independently selected from the group consisting of H, $C_1$-$C_6$ alkyl, substituted alkyl, $C_1$-$C_6$ carboxyalkyl (—(CH$_2$)$_{1-6}$COOR$^{13}$), an alpha-acyloxyalkyl, a biologically compatible salt, aryl, substituted aryl, aryl alkyl, substituted aryl alkyl, heteroaryl, and substituted heteroaryl.

The linker substituents, R, R' and R", are independently selected from the group consisting of hydrogen, alkyl, and substituted alkyl wherein n is 1-10. In addition, R" is also independently selected from the group consisting of a fluorophore, carrier molecule, solid support and reactive group.

The bridge substituents, $R^9$, $R^{10}$, $R^{11}$ and $R^{12}$, are independently selected from the group consisting of hydrogen, a reactive group, a carrier molecule, a solid support, —(CR$_2$)$_n$NR'R", —(CR$_2$)$_n$NR'-fluorophore, —(CR$_2$)$_n$-fluorophore and $C_1$-$C_6$ alkyl wherein p is 0, 1, 2 or 3. Alternatively, adjacent substituents $R^9$ and $R^{10}$ or $R^{11}$ and $R^{12}$, taken in combination, constitute a 5-membered or 6-membered alicyclic or heterocyclic ring. In one aspect a member selected from $R^9$ in combination with $R^{10}$; or $R^{11}$ in combination with $R^{12}$ together with the atoms to which they are joined, form a ring which is a 5-, or 6-membered alicyclic ring, a substituted 5-, or 6-membered alicyclic ring, a 5-, or 6-membered heterocyclic ring, or a substituted 5-, or 6-membered heterocyclic ring.

The present compounds comprise at least one linker or linker covalently bonded to a fluorophore wherein the detectable response is a result of photoinduced electron transfer (PET). In one aspect the linker has the formula —(CR$_2$)$_n$NR'R". When covalently bonded to a fluorophore the linker and reporter moiety have the formula —(CR$_2$)$_n$NR'-fluorophore. Alternatively the linker is an $C_1$-$C_{10}$ alkyl group wherein a terminal carbon atom is covalently bonded to a nitrogen atom of a reporter moiety having the formula —(CR$_2$)$_n$-fluorophore, wherein n is 1-10 for all linker formulas.

Thus, when the present compounds comprise a chelating moiety according to formula I at least one of $R_1$-$R_{12}$ is —(CR$_2$)$_n$NR'R", —(CR$_2$)$_n$NR'-fluorophore or —(CR$_2$)$_n$-fluorophore. Typically, the linker is attached to a benzene substituent wherein at least one of $R^1$-$R^8$ is —(CR$_2$)$_n$NR'R", —(CR$_2$)$_n$NR'-fluorophore or —(CR$_2$)$_n$-fluorophore. More typically at least one of $R^3$ or $R^6$ is a present linker.

Therefore, in one aspect, the present compounds have the formula:

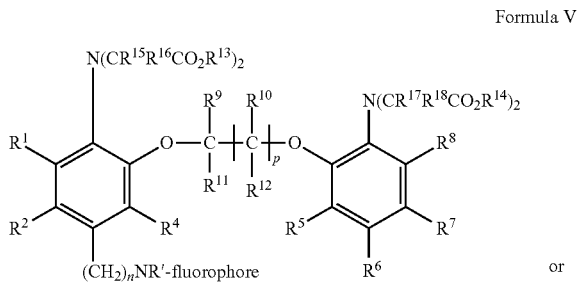

Formula V or

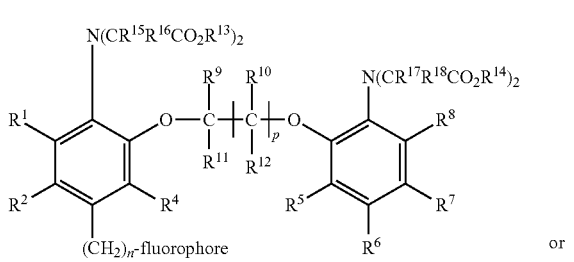

Formula VI or

-continued

Formula VII

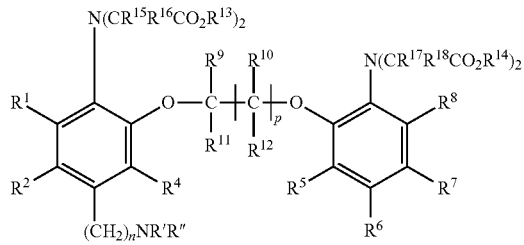

wherein $R^1$, $R^2$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R_{18}$ are as previously defined. In a further aspect, $R^5$, $R^6$, $R^7$ and $R^8$ are independently hydrogen, sulfo, alkyl or halogen, wherein the halogen is typically fluorine, chlorine or bromine. In yet a further aspect, when $R^3$ is or is attached to a present linker $R^6$ is typically an alkyl or halogen. Preferably the alkyl is methyl.

Reporter Moiety

The reporter moiety of the present invention functions as a reporter molecule to confer a detectable signal, directly or indirectly, to the target metal ions. This results in the ability to detect, monitor and quantitate target metal ions in a sample.

The present reporter molecules can be any reporter molecule known to one skilled in the art. A wide variety of chemically reactive fluorescent dyes that may be suitable for incorporation into the compounds of the invention are already known in the art (RICHARD P. HAUGLAND, MOLECULAR PROBES HANDBOOK OF FLUORESCENT PROBES AND RESEARCH PRODUCTS (2002)). Reporter moieties include, without limitation, a fluorophore, a fluorescent protein, or a tandem dye (energy transfer pair). Preferably, the reporter moiety is a fluorophore wherein when the present compounds are non-fluorescent until bound by a metal ion. After binding a metal ion and upon illumination with an appropriate wavelength the compound produces a detectable signal modulated by PET.

In one embodiment, at least one of $R^1$, $R^2$, $R^3$, $R^4$, $R^5$, $R^6$, $R^7$, $R^8$, $R^9$, $R^{10}$, $R^{11}$ and $R^{12}$ is attached to a reporter moiety via a present linker. In a particular aspect at least one of $R^1$, $R^2$, $R^3$, $R^4$, $R^5$, $R^6$, $R^7$, and $R^8$ is attached to a reporter moiety. In a preferred aspect, either $R^3$ or $R^6$ is attached to a reporter moiety.

Where the detectable response is a fluorescence response, it is typically a change in fluorescence, such as a change in the intensity, excitation or emission wavelength, distribution of fluorescence, fluorescence lifetime, fluorescence polarization, or a combination thereof. Preferably, the detectable optical response upon binding a target ion is a change in fluorescence intensity that is greater than approximately 150% relative to the same compound in the absence of the metal ion, more preferably greater than 5-fold, and most preferably more that 10-fold. In combination with the large Stokes shift of the compounds of the present invention, this large increase in fluorescent signal over baseline has not been previously observed with other calcium indicators that comprise a fluorescent PET signal mechanism. In another aspect, the detectable optical response upon binding the target metal ion is a shift in either the maximal excitation or emission wavelength or both that is greater than about 50 nm, more preferably greater than about 100 nm.

A fluorescent dye of the present invention is any chemical moiety that exhibits an absorption maximum beyond 280 nm, and when covalently linked to a metal chelating moiety of the present invention, forms a present fluorogenic metal ion-binding compound. A preferred embodiment for detecting calcium ions in live cells or calcium ions secreted from live cells is a fluorogenic calcium-binding compound wherein the reporter moiety is fluorophore. As described above, the linker is —$(CH_2)_n NR'$— or —$(CH_2)_n$—.

Dyes of the present invention include, without limitation; a pyrene, an anthracene, a naphthalene, an acridine, a stilbene, an indole or benzoindole, an oxazole or benzoxazole, a thiazole or benzothiazole, a 4-amino-7-nitrobenz-2-oxa-1, 3-diazole (NBD), a carbocyanine (including any corresponding compounds in U.S. Ser. Nos. 09/557,275; 09/968,401 and 09/969,853 and U.S. Pat. Nos. 6,403,807; 6,348,599; 5,486,616; 5,268,486; 5,569,587; 5,569,766; 5,627,027 and 6,048,982), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896), a xanthene (including any corresponding compounds disclosed in U.S. Pat. Nos. 6,162,931; 6,130,101; 6,229,055; 6,339,392; 5,451,343 and U.S. Ser. No. 09/922,333), an oxazine or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830,912), a benzofuran (including an corresponding compounds disclosed in U.S. Pat. Nos. 4,603, 209 and 4,849,362) and benzphenalenone (including any corresponding compounds disclosed in U.S. Pat. No. 4,812, 409) and derivatives thereof. As used herein, oxazines include resorufins (including any corresponding compounds disclosed in U.S. Pat. No. 5,242,805), aminooxazinones, diaminooxazines, and their benzo-substituted analogs.

Where the dye is a xanthene, the dye is optionally a fluorescein, a rhodol (including any corresponding compounds disclosed in U.S. Pat. Nos. 5,227,487 and 5,442, 045), a rosamine or a rhodamine (including any corresponding compounds in U.S. Pat. Nos. 5,798,276; 5,846,737; 5,847,162; 6,017,712; 6,025,505; 6,080,852; 6,716,979; 6,562,632). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171). Fluorinated xanthene dyes have been described previously as possessing particularly useful fluorescence properties (Int. Publ. No. WO 97/39064 and U.S. Pat. No. 6,162,931).

Preferred dyes of the invention include dansyl, xanthene, cyanine, borapolyazaindacene, pyrene, naphthalene, coumarin, oxazine and derivatives thereof. Preferred xanthenes are fluorescein, rhodamine and derivatives thereof, naphthalene and dansyl.

Typically the dye contains one or more aromatic or heteroaromatic rings, that are optionally substituted one or more times by a variety of substituents, including without limitation, halogen, nitro, sulfo, cyano, alkyl, perfluoroalkyl, alkoxy, alkenyl, alkynyl, cycloalkyl, arylalkyl, acyl, aryl or heteroaryl ring system, benzo, or other substituents typically present on chromophores or fluorophores known in the art.

In an exemplary embodiment, the dyes are independently substituted by substituents selected from the group consisting of hydrogen, halogen, amino, substituted amino, alkyl, substituted alkyl, aryl, substituted aryl, heteroaryl, substituted heteroaryl, alkoxy, sulfo, reactive group and carrier molecule. In another embodiment, the xanthene dyes of this invention comprise both compounds substituted and unsubstituted on the carbon atom of the central ring of the xanthene by substituents typically found in the xanthene-based dyes such as phenyl and substituted-phenyl moieties. Most preferred dyes are rhodamine, fluorescein, dansyl, naphthalene and derivatives thereof. The choice of the dye attached to the chelating moiety will determine the metal ion-binding compound's absorption and fluorescence emission properties as well as its live cell properties, i.e. ability to localize to mitochondria.

Selected sulfonated reporter moieties also exhibit advantageous properties, and include sulfonated pyrenes, coumarins, carbocyanines, and xanthenes (as described in U.S. Pat. Nos. 5,132,432; 5,696,157; 5,268,486; 6,130,101). Sulfonated pyrenes and coumarins are typically excited at wavelengths below about 450 nm (U.S. Pat. Nos. 5,132,432 and 5,696,157).

In an exemplary embodiment, the dye has a Stokes shift larger than about 50 nm. In a particularly useful embodiment, the dye has a Stokes shift larger than about 100 nm, more preferably larger than about 150 nm. In a further embodiment, the present compounds have a Stokes shift larger than about 200 nm, more preferably larger than about 250 nm.

Fluorescent proteins also find use as reporter moieties for the chelate compounds of the present invention. Examples of fluorescent proteins include green fluorescent protein (GFP) and the phycobiliproteins and the derivatives thereof. The fluorescent proteins, especially phycobiliproteins, are particularly useful for creating tandem dye reporter molecules. These tandem dyes comprise a fluorescent protein and a fluorophore for the purposes of obtaining a larger Stokes shift, wherein the emission spectra are farther shifted from the wavelength of the fluorescent protein's absorption spectra. This property is particularly advantageous for detecting a low quantity of a target ion in a sample wherein the emitted fluorescent light is maximally optimized; in other words, little to none of the emitted light is reabsorbed by the fluorescent protein. For this to work, the fluorescent protein and fluorophore function as an energy transfer pair wherein the fluorescent protein emits at the wavelength that the acceptor fluorophore absorbs and the fluorophore then emits at a wavelength farther from the fluorescent proteins than could have been obtained with only the fluorescent protein. Alternatively, the fluorophore functions as the energy donor and the fluorescent protein is the energy acceptor. Particularly useful fluorescent proteins are the phycobiliproteins disclosed in U.S. Pat. Nos. 4,520,110; 4,859,582; 5,055,556 and the fluorophore bilin protein combinations disclosed in U.S. Pat. No. 4,542,104. Alternatively, two or more fluorophore dyes can function as an energy transfer pair wherein one fluorophore is a donor dye and the other is the acceptor dye including any dye compounds disclosed in U.S. Pat. Nos. 6,358,684; 5,863,727; 6,372,445; 6,221,606; 6,008,379; 5,945,526; 5,863,727; 5,800,996; 6,335,440; 6,008,373; 6,184,379; 6,140,494 and 5,656,554.

The reactive group, carrier molecules, and solid support comprise a linker that is used to covalently attach the substituents to the chelating moiety or reporter moiety of the present compounds. The solid support, carrier molecule or reactive group may be directly attached (where Linker is a single bond) to the moieties or attached through a series of stable bonds. When the linker is a series of stable covalent bonds the linker typically incorporates 1-30 nonhydrogen atoms selected from the group consisting of C, N, O, S and P. When the linker is not a single covalent bond, the linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. Typically the linker incorporates less than 15 nonhydrogen atoms and are composed of any combination of ether, thioether, thiourea, amine, ester, carboxamide, sulfonamide, hydrazide bonds and aromatic or heteroaromatic bonds. Typically the linker is a combination of single carbon-carbon bonds and carboxamide, sulfonamide or thioether bonds. The bonds of the linker typically result in the following moieties that can be found in the linker: ether, thioether, carboxamide, thiourea, sulfonamide, urea, urethane, hydrazine, alkyl, aryl, heteroaryl, alkoky, cycloalkyl and amine moieties. Examples of a linker include substituted or unsubstituted polymethylene, arylene, alkylarylene, arylenealkyl, or arylthio.

In one embodiment, the linker contains 1-6 carbon atoms; in another, the linker comprises a thioether linkage. Exemplary linking members include a moiety that includes —C(O)NH—, —C(O)O—, —NH—, —S—, —O—, and the like. In another embodiment, the linker is or incorporates the formula —(CH$_2$)$_d$(CONH(CH$_2$)$_e$)$_z$— or where d is an integer from 0-5, e is an integer from 1-5 and z is 0 or 1. In a further embodiment, the linker is or incorporates the formula —O—(CH$_2$)—. In yet another embodiment, the linker is or incorporates a phenylene or a 2-carboxy-substituted phenylene.

Any combination of linkers may be used to attach the carrier molecule, solid support or reactive group and the present compounds together. The linker may also be substituted to alter the physical properties of the reporter moiety or chelating moiety, such as spectral properties of the dye.

Another important feature of the linker is to provide an adequate space between the carrier molecule, reactive group or solid support and the chelating moiety or reporter moiety so as to prevent steric hinderance. Therefore, the linker of the present compound is important for (1) attaching the carrier molecule, reactive group or solid support to the compound, (2) providing an adequate space between the carrier molecule, reactive group or solid support and the compound so as not to sterically hinder the action of the compound and (3) for altering the physical properties of the present compounds.

Reactive Groups

In another exemplary embodiment of the invention, the present compounds are chemically reactive, and are substituted by at least one reactive group. The reactive group functions as the site of attachment for another moiety, such as a carrier molecule or a solid support, wherein the reactive group chemically reacts with an appropriate reactive or functional group on the carrier molecule or solid support. Thus, in another aspect of the present invention the compounds comprise the chelating moiety, linker, reporter moiety, a reactive group moiety and optionally a carrier molecule and/or a solid support.

In an exemplary embodiment, the compounds of the invention further comprise a reactive group which is a member selected from an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a photoactivatable group, a reactive platinum complex, a silyl halide, a sulfonyl halide, and a thiol. In a particular embodiment the reactive group is selected from the group consisting of carboxylic acid, succinimidyl ester of a carboxylic acid, hydrazide, amine and a maleimide. In exemplary embodiment, at least one member selected from $R^1$, $R^2$, $R^3$, $R^4$, $R^5$, $R^6$, $R^7$, $R^8$, $R^9$, $R^{10}$, $R^{11}$, and $R^{12}$ is a reactive group. Preferably, at least one of $R^1$, $R^2$, $R^3$, $R^4$, $R^5$, $R^6$, $R^7$, and $R^8$ is a reactive group, most preferred is at least one of $R^5$, $R^6$, $R^7$ or $R^8$. Alternatively, if the present compound comprises a carrier molecule or solid support a reactive group may be covalently attached independently to those substituents, allowing for further conjugation to a reporter molecule, carrier molecule or solid support.

In one aspect, the compound comprises at least one reactive group that selectively reacts with an amine group. This amine-reactive group is selected from the group consisting of succinimidyl ester, sulfonyl halide, tetrafluorophenyl ester and iosothiocyanates. Thus, in one aspect, the present compounds form a covalent bond with an amine containing molecule in a sample. In another aspect, the compound comprises at least one reactive group that selectively reacts with a thiol group. This thiol-reactive group is selected from the group consisting of maleimide, haloalkyl and haloacetamide (including any reactive groups disclosed in U.S. Pat. Nos. 5,362,628; 5,352,803 and 5,573,904).

These reactive groups are synthesized during the formation of the present compound and carrier molecule and solid support containing compounds to provide chemically reactive metal ion-binding compounds. In this way, compounds incorporating a reactive group can be covalently attached to a wide variety of carrier molecules or solid supports that contain or are modified to contain functional groups with suitable reactivity, resulting in chemical attachment of the components. In an exemplary embodiment, the reactive group of the compounds of the invention and the functional group of the carrier molecule or solid support comprise electrophiles and nucleophiles that can generate a covalent linkage between them. Alternatively, the reactive group comprises a photoactivatable group, which becomes chemically reactive only after illumination with light of an appropriate wavelength. Typically, the conjugation reaction between the reactive group and the carrier molecule or solid support results in one or more atoms of the reactive group being incorporated into a new linkage attaching the present compound of the invention to the carrier molecule or solid support. Selected examples of functional groups and linkages are shown in Table 1, where the reaction of an electrophilic group and a nucleophilic group yields a covalent linkage.

TABLE 1

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g., succinimidyloxy (—OC$_4$H$_4$O$_2$) sulfosuccinimidyloxy (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates Choice of the reactive group used to attach the compound of the invention to the substance to be conjugated typically depends on the reactive or functional group on the substance to be conjugated and the type or length of covalent linkage desired. The types of functional groups typically present on the organic or inorganic substances (biomolecule or non-biomolecule) include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. A single type of reactive site may be available on the substance (typical for polysaccharides or silica), or a variety of sites may occur (e.g., amines, thiols, alcohols, phenols), as is typical for proteins.

Typically, the reactive group will react with an amine, a thiol, an alcohol, an aldehyde, a ketone, or with silica. Preferably, reactive groups react with an amine or a thiol functional group, or with silica. In one embodiment, the reactive group is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. No. 5,714,327.

Where the reactive group is an activated ester of a carboxylic acid, such as a succinimidyl ester of a carboxylic acid, a sulfonyl halide, a tetrafluorophenyl ester or an isothiocyanates, the resulting compound is particularly useful for preparing conjugates of carrier molecules such as proteins, nucleotides, oligonucleotides, or haptens. Where the reactive group is a maleimide, haloalkyl or haloacetamide (including any reactive groups disclosed in U.S. Pat. Nos. 5,362,628; 5,352,803 and 5,573,904 (supra)) the resulting compound is particularly useful for conjugation to thiol-containing substances. Where the reactive group is a hydrazide, the resulting compound is particularly useful for conjugation to periodate-oxidized carbohydrates and glycoproteins, and in addition is an aldehyde-fixable polar tracer for cell microinjection. Where the reactive group is a silyl halide, the resulting compound is particularly useful for conjugation to silica surfaces, particularly where the silica surface is incorporated into a fiber optic probe subsequently used for remote ion detection or quantitation.

In a particular aspect, the reactive group is a photoactivatable group such that the group is only converted to a reactive species after illumination with an appropriate wavelength. An appropriate wavelength is generally a UV wavelength that is less than 400 nm. This method provides for specific attachment to only the target molecules, either in solution or immobilized on a solid or semi-solid matrix. Photoactivatable reactive groups include, without limitation, benzophenones, aryl azides and diazirines.

Preferably, the reactive group is a photoactivatable group, succinimidyl ester of a carboxylic acid, a haloacetamide, haloalkyl, a hydrazine, an isothiocyanate, a maleimide group, an aliphatic amine, a silyl halide, a cadaverine or a psoralen. More preferably, the reactive group is a succinimidyl ester of a carboxylic acid, a maleimide, an iodoacetamide, or a silyl halide. In a particular embodiment the reactive group is a succinimidyl ester of a carboxylic acid, a sulfonyl halide, a tetrafluorophenyl ester, an iosothiocyanates or a maleimide.

Carrier Molecules

In an exemplary embodiment, the present compound is covalently bound to a carrier molecule. If the compound has a reactive group, then the carrier molecule can alternatively be linked to the compound through the reactive group. The reactive group may contain both a reactive functional moiety and a linker, or only the reactive functional moiety.

A variety of carrier molecules are useful in the present invention. Exemplary carrier molecules include antigens, steroids, vitamins, drugs, haptens, metabolites, toxins, environmental pollutants, amino acids, peptides, proteins, nucleic acids, nucleic acid polymers, carbohydrates, lipids, and polymers. In another exemplary embodiment, at least one member selected from $R^1$, $R^2$, $R^3$, $R^4$, $R^5$, $R^6$, $R^7$, $R^8$, $R^9$, $R^{10}$, $R^{11}$, and $R^{12}$, is a carrier molecule or is attached to a carrier molecule. In one aspect at least one of $R^1$, $R^2$, $R^3$, $R^4$, $R^5$, $R^6$, $R^7$, and $R^8$ is a carrier molecule or is attached to a carrier molecule. In a further aspect, at least one of $R^5$, $R^6$, $R^7$ or $R^8$ is or is a carrier molecule or is attached to a carrier molecule.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In a preferred embodiment the carrier molecule is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In another preferred embodiment, the carrier molecule is an antibody or fragment thereof, an antigen, an avidin or streptavidin, a biotin, a dextran, an IgG binding protein, a fluorescent protein, agarose, and a non-biological microparticle.

In an exemplary embodiment, the enzymatic substrate is selected from an amino acid, peptide, sugar, alcohol, alkanoic acid, 4-guanidinobenzoic acid, nucleic acid, lipid, sulfate, phosphate, —$CH_2OCO$alkyl and combinations thereof. Thus, the enzyme substrates can be cleave by enzymes selected from the group consisting of peptidase, phosphatase, glycosidase, dealkylase, esterase, guanidinobenzotase, sulfatase, lipase, peroxidase, histone deacetylase, endoglycoceramidase, exonuclease, reductase and endonuclease.

In another exemplary embodiment, the carrier molecule is an amino acid (including those that are protected or are substituted by phosphates, carbohydrates, or $C_1$ to $C_{22}$ carboxylic acids), or a polymer of amino acids such as a peptide or protein. In a related embodiment, the carrier molecule contains at least five amino acids, more preferably 5 to 36 amino acids. Exemplary peptides include, but are not limited to, neuropeptides, cytokines, toxins, protease substrates, and protein kinase substrates. Other exemplary peptides may function as organelle localization peptides, that is, peptides that serve to target the conjugated compound for localization within a particular cellular substructure by cellular transport mechanisms. Preferred protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the protein carrier molecule is an antibody, an antibody fragment, avidin, streptavidin, a toxin, a lectin, or a growth factor. Exemplary haptens include biotin, digoxigenin and fluorophores.

In another exemplary embodiment, the carrier molecule comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In another exemplary embodiment, the nucleotide carrier molecule is a nucleoside or a deoxynucleoside or a dideoxynucleoside.

Exemplary nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

In another exemplary embodiment, the carrier molecule comprises a carbohydrate or polyol that is typically a polysaccharide, such as dextran, FICOLL, heparin, glycogen, amylopectin, mannan, inulin, starch, agarose and cellulose, or is a polymer such as a poly(ethylene glycol). In a related embodiment, the polysaccharide carrier molecule includes dextran, agarose or FICOLL.

In another exemplary embodiment, the carrier molecule comprises a lipid (typically having 6-25 carbons), including glycolipids, phospholipids, and sphingolipids. Alternatively, the carrier molecule comprises a lipid vesicle, such as a liposome, or is a lipoprotein (see below). Some lipophilic substituents are useful for facilitating transport of the conjugated dye into cells or cellular organelles.

Alternatively, the carrier molecule is a cell, cellular systems, cellular fragment, or subcellular particles, including virus particles, bacterial particles, virus components, biological cells (such as animal cells, plant cells, bacteria, or yeast), or cellular components. Examples of cellular components that are useful as carrier molecules include lysosomes, endosomes, cytoplasm, nuclei, histones, mitochondria, Golgi apparatus, endoplasmic reticulum and vacuoles.

In another exemplary embodiment, the carrier molecule non-covalently associates with organic or inorganic materials. Exemplary embodiments of the carrier molecule that possess a lipophilic substituent can be used to target lipid assemblies such as biological membranes or liposomes by non-covalent incorporation of the dye compound within the membrane, e.g., for use as probes for membrane structure or for incorporation in liposomes, lipoproteins, films, plastics, lipophilic microspheres or similar materials.

In an exemplary embodiment, the carrier molecule comprises a specific binding pair member wherein the present compounds are conjugated to a specific binding pair member and used to the formation of the bound pair. Alternatively, the presence of the labeled specific binding pair member indicates the location of the complementary member of that specific binding pair; each specific binding pair member having an area on the surface or in a cavity which specifically binds to, and is complementary with, a particular spatial and polar organization of the other. In this instance, the dye compounds of the present invention function as a reporter molecule for the specific binding pair. Exemplary binding pairs are set forth in Table 2.

TABLE 2

Representative Specific Binding Pairs

| | |
|---|---|
| antigen | antibody |
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |
| peptide | peptide receptor |
| protein | protein receptor |
| enzyme substrate | enzyme |
| DNA (RNA) | cDNA (cRNA)† |
| hormone | hormone receptor |
| ion | chelator |

*IgG is an immunoglobulin
†cDNA and cRNA are the complementary strands used for hybridization Solid Supports In an exemplary embodiment, the present compounds of the invention are covalently bonded to a solid support. The solid support may be attached to the compound either through the chelating moiety, reporter moiety, or through a reactive group, if present, or through a carrier molecule, if present. Even if a reactive group and/or a carrier molecule are present, the solid support may be attached through the chelating moiety or reporter moiety. In another exemplary embodiment, at least one member selected from $R^1$, $R^2$, $R^3$, $R^4$, $R^5$, $R^6$, $R^7$, $R^8$, $R^9$, $R^{10}$, $R^{11}$, and $R^{12}$, is a solid support or is attached to a solid support. In one aspect, at least one of $R^1$, $R^2$, $R^3$, $R^4$, $R^5$, $R^6$, $R^7$, or $R^8$ is a solid support or is attached to a solid support. In a further aspect at least one of $R^5$, $R^6$, $R^7$ or $R^8$ is a solid support or is attached to a solid support.

A solid support suitable for use in the present invention is typically substantially insoluble in liquid phases. Solid supports of the current invention are not limited to a specific type of support. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like.

In some embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the compounds of the invention. Useful reactive groups are disclosed above and are equally applicable to the solid support reactive functional groups herein.

A suitable solid phase support can be selected on the basis of desired end use and suitability for various synthetic protocols. For example, where amide bond formation is desirable to attach the compounds of the invention to the solid support, resins generally useful in peptide synthesis may be employed, such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (Tenta-Gel™, Rapp Polymere, Tubingen, Germany), polydimethylacrylamide resin (available from Milligen/Biosearch, California), or PEGA beads (obtained from Polymer Laboratories).

Preparation of Conjugates

Conjugates of components (carrier molecules or solid supports), e.g., drugs, peptides, toxins, nucleotides, phospholipids and other organic molecules are prepared by organic synthesis methods using the reactive dyes of the invention, are generally prepared by means well recognized in the art (Haugland, MOLECULAR PROBES HANDBOOK, supra, (2002)). Preferably, conjugation to form a covalent bond consists of simply mixing the reactive compounds of the present invention in a suitable solvent in which both the reactive compound and the substance to be conjugated are soluble. The reaction preferably proceeds spontaneously without added reagents at room temperature or below. For those reactive compounds that are photoactivated, conjugation is facilitated by illumination of the reaction mixture to activate the reactive compound. Chemical modification of water-insoluble substances, so that a desired compound-conjugate may be prepared, is preferably performed in an aprotic solvent such as dimethylformamide, dimethylsulfoxide, acetone, ethyl acetate, toluene, or chloroform. Similar modification of water-soluble materials is readily accomplished through the use of the instant reactive compounds to make them more readily soluble in organic solvents.

Preparation of peptide or protein conjugates typically comprises first dissolving the protein to be conjugated in aqueous buffer at about. 1-10 mg/mL at room temperature or below. Bicarbonate buffers (pH about 8.3) are especially suitable for reaction with succinimidyl esters, phosphate buffers (pH about 7.2-8) for reaction with thiol-reactive functional groups and carbonate or borate buffers (pH about 9) for reaction with isothiocyanates and dichlorotriazines. The appropriate reactive compound is then dissolved in a nonhydroxylic solvent (usually DMSO or DMF) in an amount sufficient to give a suitable degree of conjugation when added to a solution of the protein to be conjugated. The appropriate amount of compound for any protein or other component is conveniently predetermined by experimentation in which variable amounts of the compound are added to the protein, the conjugate is chromatographically purified to separate unconjugated compound and the compound-protein conjugate is tested in its desired application.

Following addition of the reactive compound to the component solution, the mixture is incubated for a suitable period (typically about 1 hour at room temperature to several hours on ice), the excess compound is removed by gel filtration, dialysis, HPLC, adsorption on an ion exchange or hydrophobic polymer or other suitable means. The compound-conjugate is used in solution or lyophilized. In this way, suitable conjugates can be prepared from antibodies, antibody fragments, avidins, lectins, enzymes, proteins A and G, cellular proteins, albumins, histones, growth factors, hormones, and other proteins.

Conjugates of polymers, including biopolymers and other higher molecular weight polymers are typically prepared by means well recognized in the art (for example, Brinkley et al., *Bioconjugate Chem.*, 3: 2 (1992)). In these embodiments, a single type of reactive site may be available, as is typical for polysaccharides) or multiple types of reactive sites (e.g. amines, thiols, alcohols, phenols) may be available, as is typical for proteins. Selectivity of labeling is best obtained by selection of an appropriate reactive dye. For example, modification of thiols with a thiol-selective reagent such as a haloacetamide or maleimide, or modification of amines with an amine-reactive reagent such as an activated ester, acyl azide, isothiocyanate or 3,5-dichloro-2,4,6-triazine. Partial selectivity can also be obtained by careful control of the reaction conditions.

When modifying polymers with the compounds, an excess of compound is typically used, relative to the expected degree of compound substitution. Any residual, unreacted compound or a compound hydrolysis product is typically removed by dialysis, chromatography or precipitation. Presence of residual, unconjugated dye can be detected by thin layer chromatography using a solvent that elutes the dye away from its conjugate. In all cases it is usually preferred that the reagents be kept as concentrated as practical so as to obtain adequate rates of conjugation.

In an exemplary embodiment, the conjugate of the invention is associated with an additional substance, that binds either to the fluorophore or the conjugated substance (carrier molecule or solid support) through noncovalent interaction. In another exemplary embodiment, the additional substance is an antibody, an enzyme, a hapten, a lectin, a receptor, an oligonucleotide, a nucleic acid, a liposome, or a polymer. The additional substance is optionally used to probe for the location of the dye-conjugate, for example, as a means of enhancing the signal of the dye-conjugate.

Synthesis

Typically the synthetic methodology used to prepare the compounds of the invention involves preparation of an alkylene linker directly attached to one of the phenyl ring carbons of the chelator moiety by a carbon-carbon bond. This can be achieved by a variety of synthetic operations. Preparation of this linker is done in such as way so as to include a nucleophilic or pro-nucleophilic moiety attached to the linker. The nucleophilic moiety on the linker is then covalently attached to a fluorophore by alkylation or acylation with a reactive electrophilic version of the fluorophore. The order of attachment can be reversed, i.e. the linker-fluorophore combination can be prepared first, followed by attachment to the chelator.

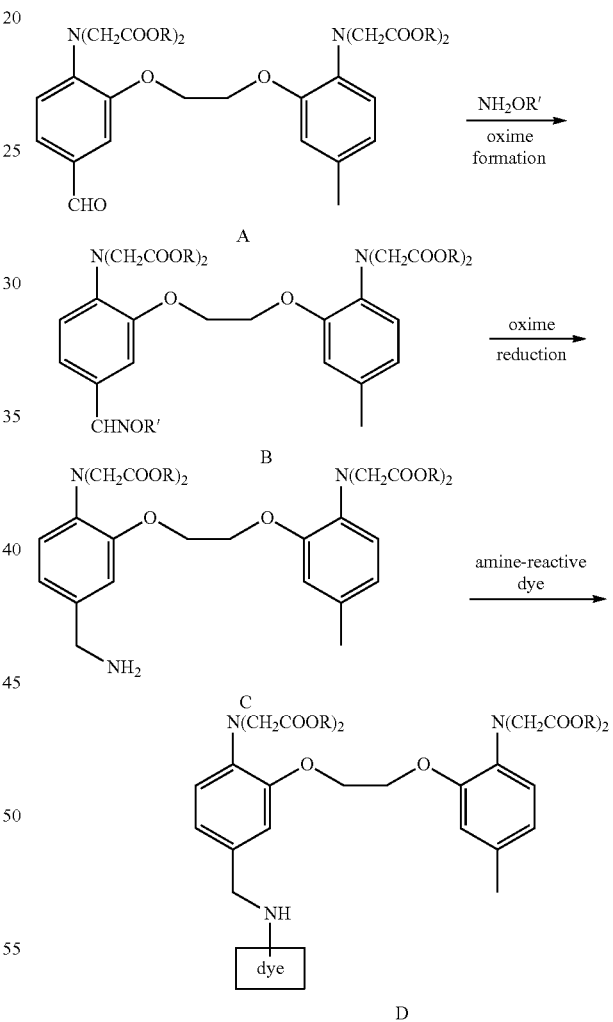

Method of Use

The metal ion chelating compounds of the invention are useful for any application where it is desirable to complex a target metal ion. Selected compounds of the invention may be useful as ionophores, that is, they facilitate the transport of selected target ions across cell membranes. Where the present compound is bound to a conjugated substance that is a polymeric matrix, such as a microparticle, or agarose, the compounds are useful for depleting a sample solution of a selected target ion, particularly where the polymeric matrix is used to pack a chromatography column. Other compounds (those bound to a reporter moiety) are useful as fluorescent indicators for a selected target ion.

In order for a particular indicator of the present invention to be useful for detection purposes, it must exhibit a detectable change in spectral properties upon complexation of the desired metal ion (target ion) in the chelating moiety. Preferably the change in spectral properties is a change in fluorescence properties. More preferably, the instant indicators display an intensity increase or decrease in emission energy upon the complexation of the desired target ion.

The present compounds are useful for binding target ions resulting in a complex of the target ion and the present compounds. Therefore, an additional aspect of the invention includes the compound of the invention further comprising a metal ion that is associated and/or complexed within the chelate portion of the compound. The metal ion is optionally $Ca^{2+}$, $Zn^{2+}$, $Mg^{2+}$, $Ga^{3+}$, $Tb^{3+}$, $La^{3+}$, $Pb^{2+}$, $Hg^{2+}$, $Cd^{2+}$, $Cu^{2+}$, $Ni^{2+}$, $Co^{2+}$, $Fe^{2+}$, $Mn^{2+}$, $Ba^{2+}$, and $Sr^{2+}$.

Preferably the complex comprises physiological relevant cations such as $Ca^{2+}$, $Mg^{2+}$, $Fe^{2+}$ and $Zn^{2+}$.

Accordingly, a method for binding target metal ions in a sample comprises the following steps:
a) contacting the sample with a fluorogenic chelate compound of the present invention to form a contacted sample; and,
b) incubating the contacted sample for a sufficient amount of time to allow the compound to bind the target metal ion whereby the metal ion is bound.

When the present compounds are used as indicators a reporter moiety is covalently attached to the chelate moiety via a present PET linker. The sample is illuminated with an appropriate wavelength whereby the target ion is detected. In such an assay the target ion can also be quantitated and monitored.

The specific indicator used in an assay or experiment is selected based on the desired affinity for the target ion as determined by the expected concentration range in the sample, the desired spectral properties, and the desired selectivity. Initially, the suitability of a material as an indicator of ion concentration is commonly tested by mixing a constant amount of the indicating reagent with a measured amount of the target ion under the expected experimental conditions.

Preferred indicators display a high selectivity, that is, they show a sufficient rejection of non-target ions. The interference of a non-target ion is tested by a comparable titration of the indicator with that ion. Although preferred target ions for most indicators of the present invention are $Ca^{++}$, $Na^+$ and $K^+$, any ion that yields a detectable change in absorption wavelengths, emission wavelengths, fluorescence lifetimes or other measurable optical property over the concentration range of interest is potentially measured using one of the indicators of this invention. Most preferred is calcium ions.

The indicator is generally prepared for use as a detection reagent by dissolving the indicator in solution at a concentration that is optimal for detection of the indicator at the expected concentration of the target ion. Modifications that are designed to enhance permeability of the indicator through the membranes of living cells, such as acetoxymethyl esters and acetates, may require the indicator to be predissolved in an organic solvent such as dimethylsulfoxide (DMSO) before addition to a cell suspension, where the indicators then readily enter the cells. Intracellular enzymes cleave the esters to the more polar acids and phenols that are then well retained inside the cells. For applications where permeability of cell-membranes is required, the indicators of the invention are typically substituted by only one fluorophore.

Therefore, a method for binding and detecting target ions in a live cell comprises the following steps:
a) contacting a sample of live cells with a present compound with the proviso that at least one of $R^{13}$ or $R^{14}$ is —$CH_2OCOalkyl$ or $CH_3$;
b) incubating the sample and the compound for sufficient time to allow the compound to chelate the target metal ion; and,
c) illuminating the sample with an appropriate wavelength to generate a detectable fluorescent signal that is modulated by PET whereby the target ion is detected in a live cell.

A specific indicator of the present invention is useful for the detection and/or quantification of a desired target ion, when the binding of the target ion in the metal ion-binding moiety of the indicator results in a detectable change in spectral properties. Preferably, the change in spectral properties is a detectable fluorescence response.

The optical response of the indicating reagent is determined by changes in absorbance or fluorescence, preferably fluorescence. If absorbance measurements are used to determine ion concentrations, then it is usually optimal to adjust the optical density of the indicator in the sample over the range of analyte concentration to a value of approximately 0.02 to 2.5 (most preferably 0.1 to 1). For fluorescence measurements, the concentration of the indicator will depend mostly on the sensitivity of the equipment used for its detection.

If the optical response of the indicator will be determined using fluorescence measurements, samples are typically stained with indicator concentrations of $10^{-9}$ M to $10^{-2}$ M. The most useful range of analyte concentration is about one log unit above and below the dissociation constant of the ion-indicator complex. This dissociation constant is determined by titration of the indicator with a known concentration of the target ion, usually over the range of virtually zero concentration to approximately 100 millimolar of the target ion, depending on which ion is to be measured and which indicator is being used. The dissociation constant may be affected by the presence of other ions, particularly ions that have similar ionic radii and charge. It may also be affected by other conditions such as ionic strength, pH, temperature, viscosity, presence of organic solvents and incorporation of the sensor in a membrane or polymeric matrix, or conjugation or binding of the sensor to a protein or other biological molecule. Any or all of these effects need to be taken into account when calibrating an indicator.

The indicator is combined with a sample in a way that will facilitate detection of the target ion concentration in the sample. The sample is generally a representative cell population, fluid or liquid suspension that is known or suspected to contain the target ion. Representative samples include intracellular fluids such as in blood cells, cultured cells, muscle tissue, neurons and the like; extracellular fluids in areas immediately outside of cells; in vesicles; in vascular tissue of plants and animals; in biological fluids such as blood, saliva, and urine; in biological fermentation media; in environmental samples such as water, soil, waste water and sea water; in industrial samples such as pharmaceuticals, foodstuffs and beverages; and in chemical reactors. Detection and quantitation of the target ion in a sample can help characterize the identity of an unknown sample, or facilitate quality control of a sample of known origin.

In one embodiment of the invention, the sample contains cells, and the indicator is combined with the sample in such a way that the indicator is present within the sample cells. By selection of the appropriate chelating moiety, fluorophore, and the substituents thereon, indicators are prepared that will selectively localize in desired organelles, and provide measurements of the target ion in those organelles. Conjugates of the indicators of the invention with organelle-targeting peptides are used to localize the indicator to the selected organelle, facilitating measurement of target ion presence or concentration within the organelle (as described in U.S. Pat. No. 5,773,227). Alternatively, selection of a lipophilic fluorophore, or a fluorophore having predominantly lipophilic substituents will result in localization in lipophilic environments in the cell, such as cell membranes. Selection of cationic indicators will typically result in localization of the indicator in mitochondria.

In another aspect of the invention, a composition of matter comprises any of the compounds described above, and optionally includes a metal ion. In one embodiment, the compounds of the invention, in any of the embodiments described above, are associated, either covalently or noncovalently, with a surface such as a microfluidic chip, a silicon chip, a microscope slide, a microplate well, or another solid matrix, and is combined with the sample of interest as it flows over the surface. The detectable optical response is therefore detected on the matrix surface itself, typically by use of an instrumental. This embodiment of the invention is particularly suited to high-throughput screening using automated methods.

Quantification of target ion levels in samples is typically accomplished using the indicators of the present invention by methods known in the art. For example, the ratiometric measurement of ion concentration provides accurate measurement of ion concentrations by the treatment of the fluorescence data as the ratio of excitation or fluorescence intensities at two wavelengths, rather than the absolute intensity at a single wavelength. Using the ratio method, a number of variables that may perturb the ion concentration measurements are eliminated. In particular, ion-dependent factors that affect the signal intensity, such as nonuniform intracellular dye concentrations, probe leakage, dye bleaching and cell thickness, are canceled in the ratio measurements, since these parameters have a similar effect on intensities at both wavelengths. While the ratio method can be used to determine concentrations using observation of either the excitation spectra of the indicator, the emission spectra of the indicator, or both, in the case of the indicators of the present invention, the shift in excitation energy upon binding metal ions makes observation of the excitation spectrum a more useful technique. In either case, to achieve maximal utility, the indicator must be calibrated (to compensate for variance in the dissociation constant of the indicator due to ionic strength, viscosity, or other conditions within the sample). To calibrate the indicator, ionophores such as A-23187, gramicidin, valinomycin, or ionomycin are used. Non-ratiometric analysis can also be accomplished by calibration with a second fluorescent dye present in the sample.

The optical response of the indicator to the ion can be detected by various means that include measuring absorbance or fluorescence changes with an instrument, visually, or by use of a fluorescence sensing device. Several examples of fluorescence sensing devices are known, such as fluorometers, fluorescence microscopes, laser scanners, flow cytometers, and microfluidic devices, as well as by cameras and other imaging equipment. These measurements may be made remotely by incorporation of the fluorescent ion sensor as part of a fiber optic probe. The indicator is covalently attached to the fiber optic probe material, typically glass or functionalized glass (e.g., aminopropyl glass) or the indicator is attached to the fiber optic probe via an intermediate polymer, such as polyacrylamide. The indicator solution is alternatively incorporated non-covalently within a fiber optic probe, as long as there is a means whereby the target ion can come into contact with the indicator solution.

C. Kits of the Invention

Due to the advantageous properties and the simplicity of use of the instant metal ion-binding compounds, they are particularly useful in the formulation of a kit for the complexation, detection, quantification or monitoring of selected target ions, comprising one or more compounds or compositions of the invention in any of the embodiments described above (optionally in a stock solution), instructions for the use of the crown ether compound to complex or detect a desired target ion, and optionally comprising additional components. In one aspect, the compounds of the invention are associated with a surface, such as a chip, microplate well, or other solid matrix, and the sample of interest flows over the surface. The detectable optical response is therefore detected on the matrix surface itself.

Therefore a kit of the present invention for binding a target metal ion in a sample comprises a present compound and instructions for use thereof. The kit may further comprise one or more components selected from the group consisting of a calibration standard of a metal ion, an ionophore, a fluorescent standard, an aqueous buffer solution and an organic solvent.

The additional kit components may be selected from, without limitation, calibration standards of a target ion, ionophores, fluorescence standards, aqueous buffers, and organic solvents. The additional kit components are present as pure compositions, or as aqueous solutions that incorporate one or more additional kit components. Any or all of the kit components optionally further comprise buffers.

The examples below are given so as to illustrate the practice of this invention. They are not intended to limit or define the entire scope of this invention.

EXAMPLES

Example 1. Synthesis of 5-(Aminomethyl) BAPTA

To a stirred suspension of 5-formyl BAPTA 1 (5.60 g, 10 mmol) in EtOH (100 mL) was added a solution of hydroxylamine hydrochloride (1.40 g, 20 mmol) in $H_2O$ (5 mL) followed by 3N NaOAc (5 mL, 15 mmol). The mixture was stirred at 60° C. for 4 h, cooled to room temperature and evaporated. Water (200 mL) was added to the residue, the product filtered and washed with water (10×50 mL), dried in air, then in vacuo to give oxime 2, 5.37 g (91%) as an off-white solid. The product 2 does not require purification to use in the next step.

To a stirred solution of oxime 2 (4.71 g, 8 mmol) in acetic acid (80 mL), powdered Zn (2.62 g, 40 mmol) was added in one portion. The mixture was stirred for 6 h, diluted with $CHCl_3$ (300 mL) and filtered from inorganic material. The filtrate was evaporated and the residue loaded onto a $SiO_2$ column (3×30 cm bed, made in 5% MeOH and 1% AcOH in $CHCl_3$). The product was eluted with a gradient of 5-20% MeOH in $CHCl_3$ with 1% AcOH to give the amine 3, 2.72 g (59%) as an off-white solidified oil.

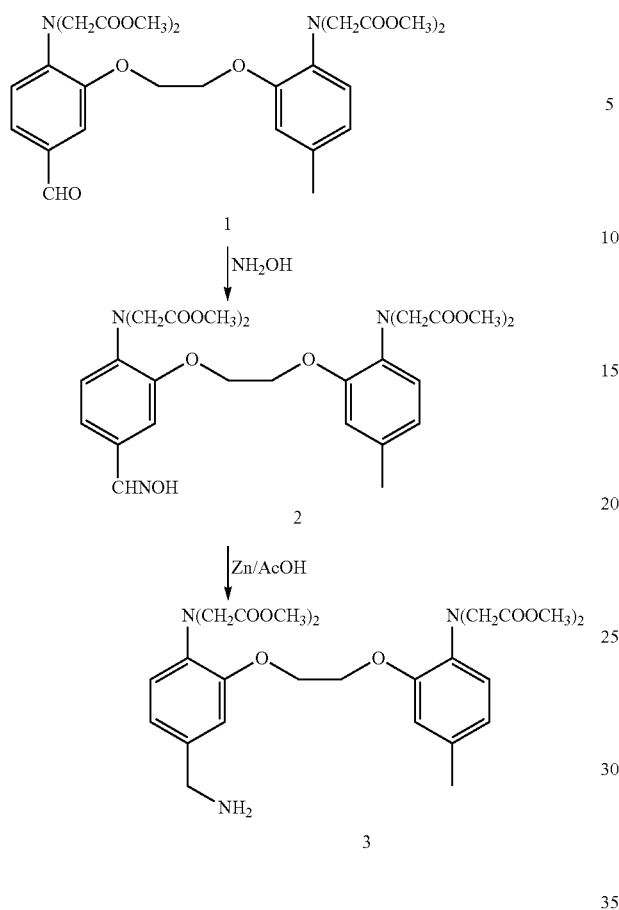
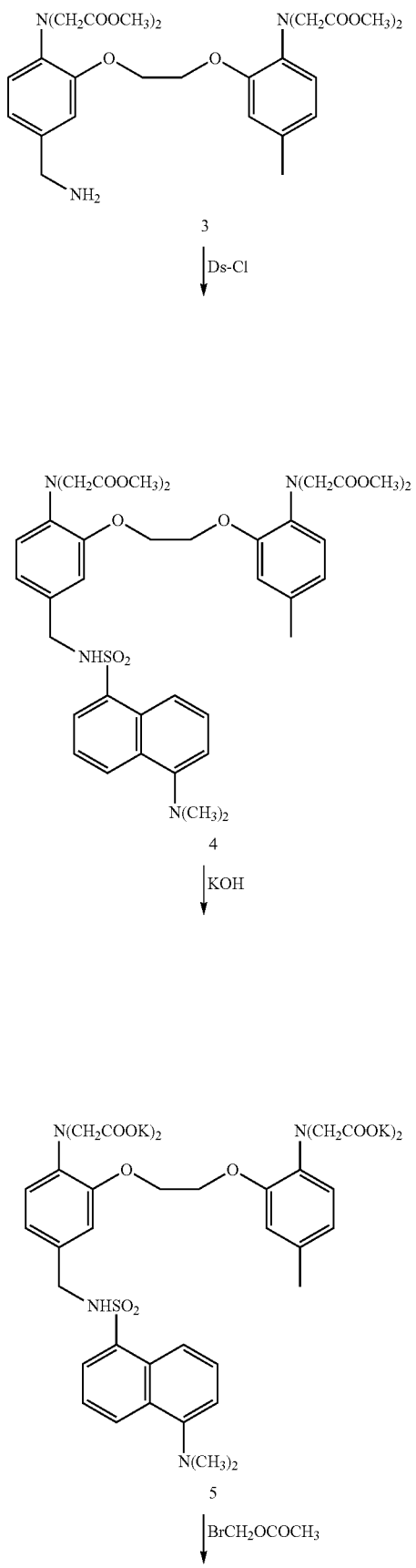

Example 2: Synthesis of 5-(Dansylaminomethyl) BAPTA derivatives

To a solution of amine 3 (160 mg, 0.28 mmol) in pyridine (3 mL), dry powdered dansyl chloride (98 mg, 0.36 mmol) was added in three portions within 5 min. The mixture was stirred for 2 h, then evaporated. The solid residue was dissolved in CHCl$_3$ (100 mL), washed with H$_2$O (100 mL), 1% AcOH (2×100 mL), and sat. NaCl (100 mL). Chloroform was evaporated and the residue was purified by preparative TLC on silica gel using 3% MeOH in CHCl$_3$ as eluant to give 5-(dansylaminomethyl) BAPTA, tetramethyl ester 4, 60 mg (27%) as a white powder.

A mixture of tetramethyl ester 4 (60 mg, 0.074 mmol), MeOH (1 mL), dioxane (1 mL), H$_2$O (1 mL), and 1N KOH (0.75 mL, 0.75 mmoL) was stirred for 16 h, then 0.2 N HCl added to achieve pH 9.5, and the mixture was evaporated. The residue was purified by column chromatography on Sephadex LH-20 (3.5×50 cm bed, made in H$_2$O) using H$_2$O as eluant to give 5-(dansylaminomethyl) BAPTA, tetrapotassium salt 5, 46 mg (69%) as an off-white solid after lyophilization.

A mixture of compound 5 (9 mg, 0.01 mmol), bromomethyl acetate (10 μL, 0.1 mmol), and N,N-diisopropylethylamine (DIEA, 35 μL, 0.2 mmol) in DMF (0.3 mL) was stirred for 1 h, and evaporated. The residue was purified by preparative TLC on silica gel using 2% MeOH in CHCl$_3$ as eluant to give 5-(dansylaminomethyl) BAPTA, tetra(acetoxymethyl) ester 6, 5 mg (48%) as an off-white solid.

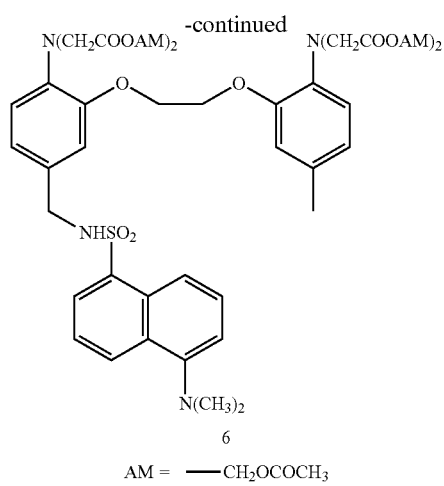

Example 3: Synthesis of 5-(N-(5'-fluoresceinyl)aminomethyl) derivatives

To a stirred solution of amine 3 (115 mg, 0.2 mmol) and DIEA (0.17 mL, 1.0 mmol) in $CH_2Cl_2$ (5 mL) was added a solution of acyl chloride 8, prepared from the acid 7 (149 mg, 0.3 mmol) and oxalyl chloride (0.1 mL, 1.2 mmol). The mixture was stirred 16 h, then diluted with $CHCl_3$ (100 mL), and washed with 1% AcOH (2×20 mL), sat. NaCl, filtered and evaporated. The residue was purified by preparative TLC on silica gel using 5% MeOH in $CHCl_3$ as eluant to give tetramethyl ester 9, 71 mg (34%) as an off-white solid.

A mixture of tetramethyl ester 9 (50 mg, 0.047 mmol), MeOH (2 mL), dioxane (2 mL), and 1N KOH (0.5 mL, 0.5 mmoL) was stirred for 16 h, then 0.2 N HCl added to pH 9.0, and the mixture was evaporated. The residue was purified by column chromatography on Sephadex LH-20 (6×70 cm bed, made in $H_2O$) using $H_2O$ as eluant to give hexapotassium salt 10, 39 mg (72%) as a yellow solid (after lyophilization).

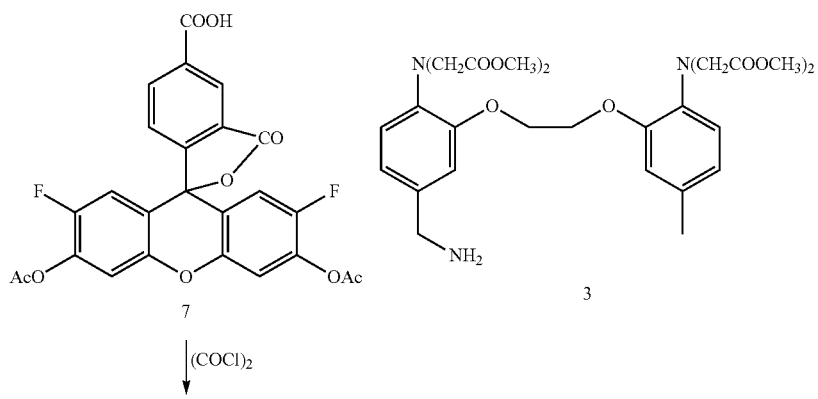

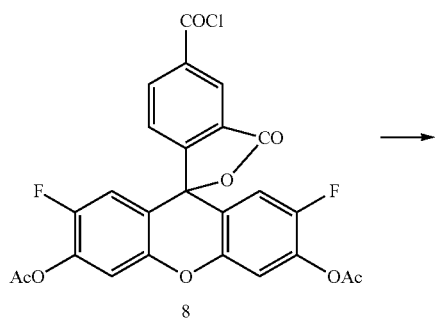

-continued

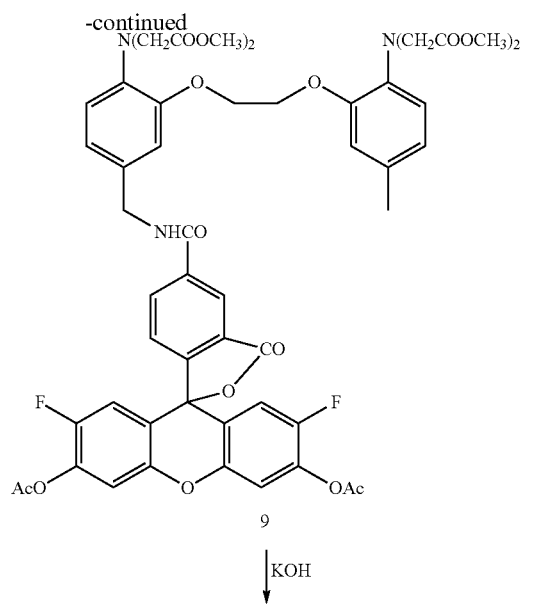

9

↓ KOH

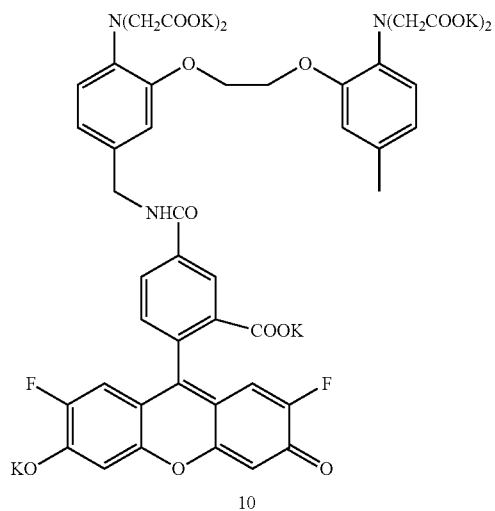

10

Example 4: Synthesis of 5-(1,8-naphthaleneimidomethyl) BAPTA derivatives

A mixture of amine 3 (1.46 g, 2.5 mmol) and 4-amino-1,8-naphthalic anhydride 11 (0.64 g, 3.0 mmol) in DMF (10 mL) was stirred at 60° C. for 20 h, cooled to room temperature and diluted with CHCl$_3$ (400 mL). The mixture was washed with sat. NaHCO$_3$ (5×500 mL), H$_2$O (500 mL), sat. NaCl (500 mL), filtered and evaporated. The residue was purified by chromatography on a silica gel column (6×50 cm bed, made with 45% EtOAc in hexanes) using an EtOAC gradient (45-70%) in hexanes to give compound 12, 0.26 g (14%) as a yellow solid.

A solution of tetramethyl ester 12 (210 mg, 0.27 mmol) in MeOH (30 mL) and 1N KOH (2.7 mL, 1.0 mmoL) was stirred for 16 h, then 0.2 N HCl was added to pH 8.5 and the mixture was evaporated. The residue was purified by column chromatography on Sephadex LH-20 (6×70 cm bed, made in H$_2$O) using H$_2$O as eluant to give tetrapotassium salt 13, 210 mg (89%) as a yellow solid after lyophilization.

A solution of tetramethyl ester 12 (77 mg, 0.1 mmol) in MeOH (1 mL), dioxane (2 mL), and 1N KOH (1.0 mL, 1.0 mmoL) was stirred for 16 h, then evaporated. The residue was dissolved in H$_2$O (10 mL) and 0.2 N HCl was added to pH 3.5. The resulting precipitate was filtered, washed with cold water (3 mL), and dried in vacuo to give compound 14 58 mg (80%) as an orange solid. Tetraacid 14 was used in the next step without purification.

A mixture of compound 14 (44 mg, 0.05 mmol), bromomethyl acetate (50 μL, 0.5 mmol) and N,N-diisopropylethylamine (175 μL, 1.0 mmol) in DMF (2 mL) was stirred for 16 h and evaporated. The residue was purified by preparative TLC on silica gel using 50% EtOAc in hexanes as eluant to give tetra(acetoxymethyl) ester 15, 26 mg (52%) as an orange solid.

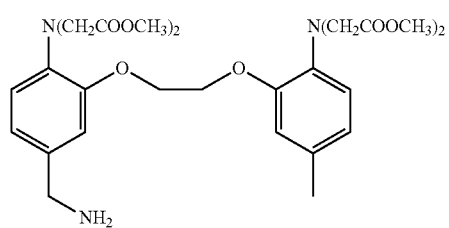

3

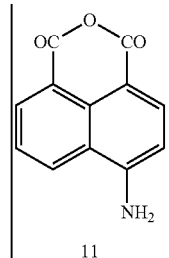

11

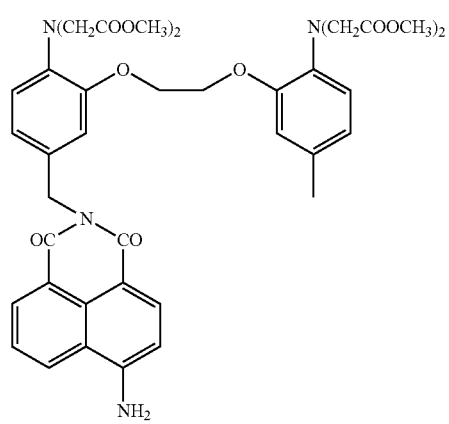

12

↓ KOH

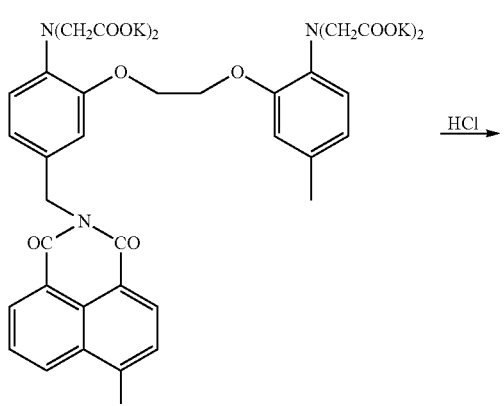

13

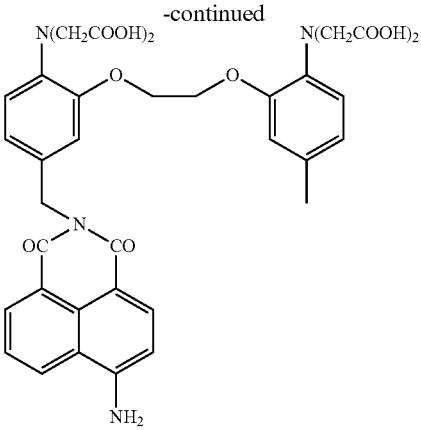

14

↓

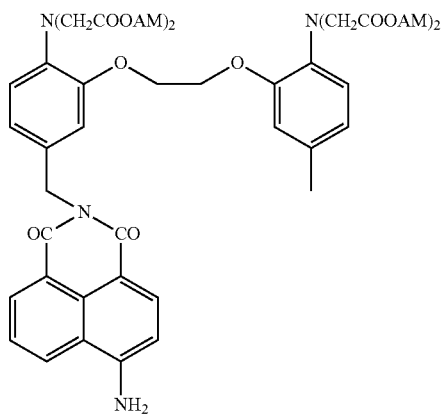

15

AM = —CH₂OCOCH₃

Example 5: Synthesis of
5-(N-(resorufinyl)aminomethyl) BAPTA derivatives

To a stirred solution of amine 3 (115 mg, 0.2 mmol) and DIEA (0.17 mL, 1.0 mmol) in DMF (2 mL) was added a solution of (N-hydroxysuccinimidylcarboxy)resorufin 16 (50 mg, 0.14 mmol) in DMF (2 mL). The mixture was stirred 16 h, then diluted with CHCl₃ (100 mL), and washed with 1% AcOH (3×50 mL), sat. NaCl (100 mL), filtered and evaporated. The residue was purified by preparative TLC on silica gel using 5% MeOH and 1% AcOH in CHCl₃ as eluant to give tetramethyl ester 17, 80 mg (70%) as a dark red solid.

A mixture of tetramethyl ester 17 (80 mg, 0.1 mmol) and LiI (1.340 g, 10 mmoL) in anhydrous acetonitrile (10 mL) was refluxed for 16 h. The resulted dark solution was cooled to room temperature and the crude product was collected by filtration and washed with acetonitrile (5×5 mL). It was purified by column chromatography on Sephadex LH-20 (2.6×90 cm bed, made in H₂O) using H₂O as eluant to give tetralithium salt 18, 15 mg (19%) as a dark purple solid (after lyophilization).

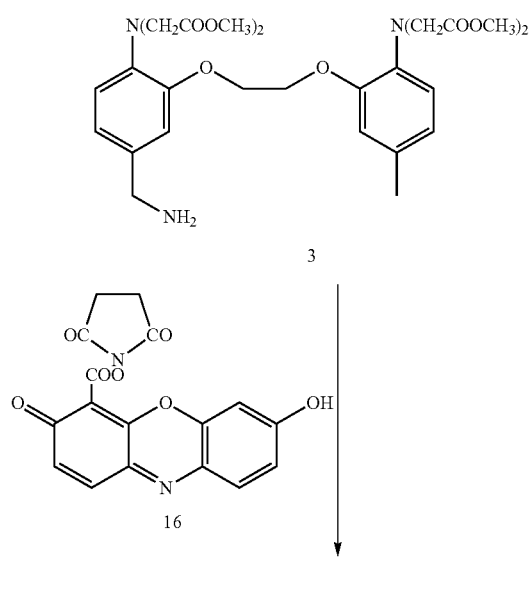

Example 6: Synthesis of 5-(N-(azarhodol)aminomethyl) BAPTA derivatives

To a stirred solution of amine 3 (58 mg, 0.1 mmol) and DIEA (0.09 mL, 0.5 mmol) in DMF (3 mL) was added a solution of (N-hydroxysuccinimidylcarboxy)azarhodol 19 (40 mg, 0.1 mmol). The mixture was stirred 6 h, then diluted with $CHCl_3$ (100 mL), and washed with 1% AcOH (3×100 mL), water (2×100 mL), sat. NaCl (100 mL), filtered and evaporated. The residue was purified by preparative TLC on silica gel using 5% MeOH and 2% AcOH in $CHCl_3$ as eluant to give tetramethyl ester 20, 45 mg (54%) as a dark blue solid.

A mixture of tetramethyl ester 20 (20 mg, 0.024 mmol) and LiI (319 mg, 2.4 mmoL) in anhydrous acetonitrile (5 mL) was refluxed for 16 h. The resulted dark solution was cooled to room temperature and the crude product was collected by filtration and washed with acetonitrile (5×5 mL). It was purified by column chromatography on Sephadex LH-20 (1.7×70 cm bed, made in $H_2O$) using $H_2O$ as eluant to give tetralithium salt 21, 13 mg (67%) as a dark purple solid (after lyophilization).

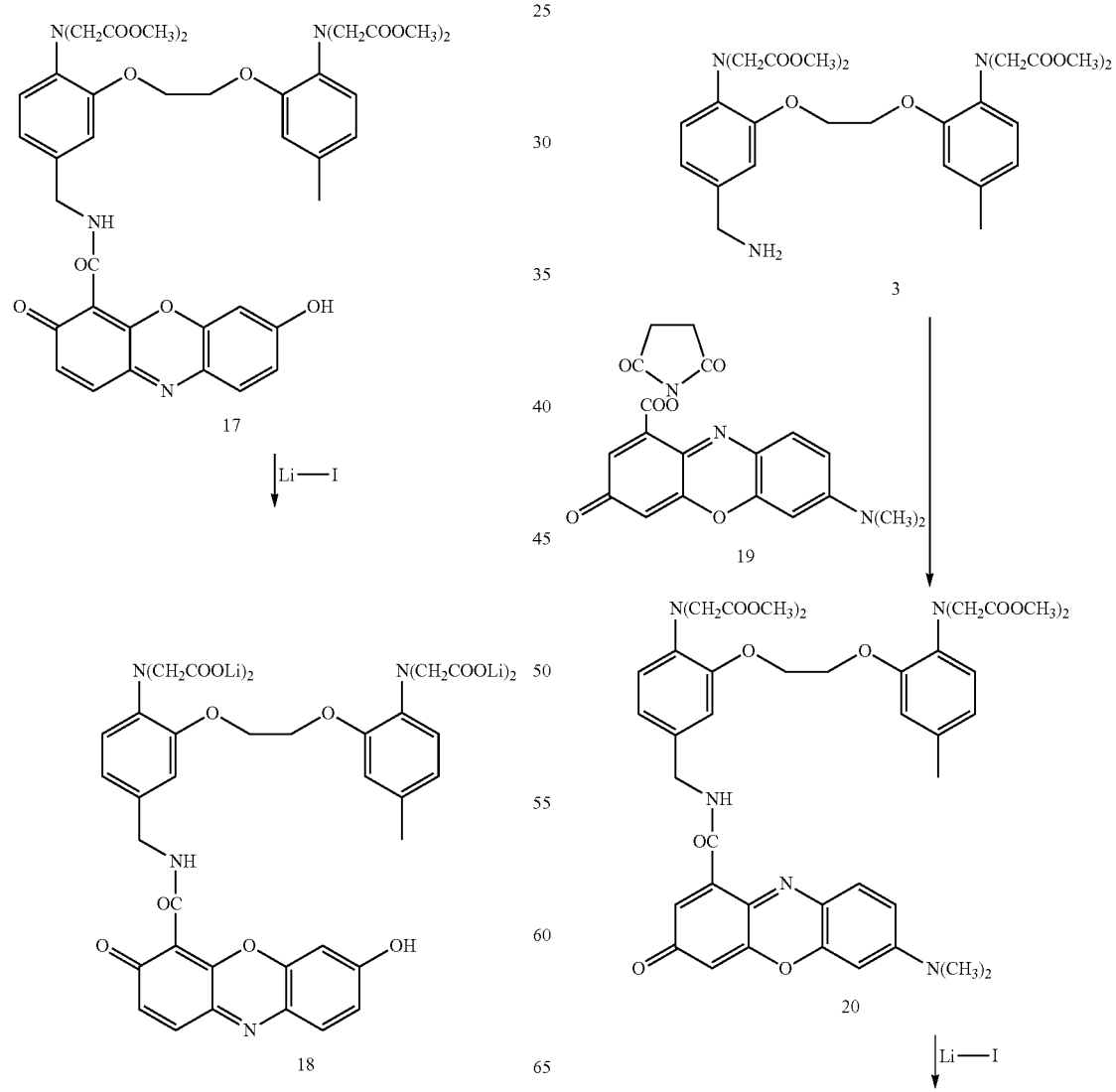

-continued

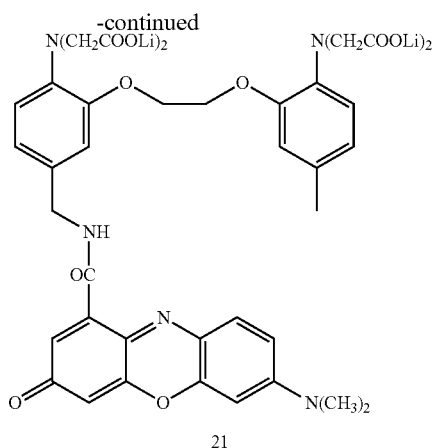

21

Example 7: Calcium Binding of Certain Calcium Binding Compounds

In all cases, samples were dissolved in nanopure(np)-$H_2O$ at concentrations of approximately 1 mg/mL, except Compound 18 which was dissolved in 1:1 DMSO:npH2O. Non-quantitative aliquots of these solutions were added to approximately 3 mL of 39 μM Ca++ buffer, 100 mM KCl, 30 mM MOPS (pH7.2) (Compounds 5, 10, 13), Zero Ca++ buffer, 100 mM KCl, 30 mM MOPS (pH7.2) (Compound 18), or npH2O (Compound 21). Absorption spectra were obtained using a Perkin Elmer UV/Vis Spectrometer (Lambda 35 or 40). Fluorescence samples were prepared by pipetting aliquots of respective stock solutions to a series of disposable cuvettes containing 2 mL of Ca++ buffers from Calcium Calibration Buffer Kit #2 (Invitrogen cat.#3009) (0-39 μM). The final concentration of compound ranged from approximately 0.1-4 μM. Samples were excited at their wavelength of maximum absorption and spectra were obtained using a Perkin Elmer Luminescence Spectrometer (LS50B, LS55). Emission intensities were recorded at the respective maxima and Kd values calculated. See Table 2.

TABLE 2

Binding properties of the certain calcium binding compounds

| Compound | Fluorophore | $\lambda_{ex}$ (nm) | $\lambda_{em}$ (nm) | $K_d$ (Ca), nM | $\Delta F = Fb/Fo^i$ |
|---|---|---|---|---|---|
| 5 | Dansyl | 331 | 549 | 81 | 3 |
| 10 | Oregon Green | 494 | 522 | 86 | 2 |
| 13 | Lucifer Yellow | 432 | 550 | 161 | 12 |
| 18 | Resorufin | 550 | 589 | 271 | 5 |
| 21 | AzaRhodol | 612 | 641 | 219 | 11 |

All patents and patent applications referred to within this document are incorporated by reference to the same extent as if each individual publication, patent or patent application was specifically and individually indicated to be incorporated by reference.

The reagents employed in the examples are commercially available or can be prepared using commercially available instrumentation, methods, or reagents known in the art. The foregoing examples illustrate various aspects of the invention and practice of the methods of the invention. The examples are not intended to provide an exhaustive description of the many different embodiments of the invention. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

What is claimed is:

1. A compound for the detection of metal ions wherein a detectable response is modulated by photoinduced electron transfer (PET), wherein the compound comprises a fluorescent protein that is covalently bonded to the metal chelating moiety by a linker,
—$(CR_2)_n NR'$—, wherein R and R' are independently hydrogen, alkyl, or substituted alkyl and n is 1-10;
or —$(CR_2)_n$— wherein R is alkyl or substituted alkyl and n=1-10;
or $(CH_2)_p$ wherein p is 2-10.

2. A composition comprising:
a) the compound of claim 1; and,
b) a metal ion that is capable of being chelated by the compound.

3. The composition of claim 2, wherein the metal ion is selected from the group consisting of $Ca^{2+}$, $Zn^{2+}$, $Mg^{2+}$, $Ga^{3+}$, $Tb^{3+}$, $La^{3+}$, $Pb^{2+}$, $Hg^{2+}$, $Cd^{2+}$, $Cu^{2+}$, $Ni^{2+}$, $Co^{2+}$, $Fe^{2+}$, $Mn^{2+}$, $Ba^{2+}$, and $Sr^{2+}$.

4. A method for binding a target metal ion in a sample, comprising steps of:
a. contacting the sample with the metal ion binding compound of claim 1 to form a contacted sample; and,
b. incubating the contacted sample for sufficient time to allow the metal ion binding compound to chelate the target metal ion whereby the metal ion is bound.

5. The method of claim 4, wherein the sample comprises live cells, intracellular fluids, extracellular fluids, biological fluids, biological fermentation media, environmental sample, industrial samples, proteins, peptides, buffer solutions or biological fluids or chemical reactors.

6. The method of claim 4, wherein the sample comprises blood cells, immune cells, cultured cells, muscle tissue, neurons, extracellular vesicles; vascular tissue, blood fluids, saliva, urine; water, soil, waste water, sea water; pharmaceuticals, foodstuffs or beverages.

7. The method of claim 4, wherein the method further comprises detecting a target metal ion wherein the sample is illuminated with an appropriate wavelength whereby the target metal ion is detected.

8. The method of claim 4, wherein the metal ion is $Ca^{2+}$, $Zn^{2+}$, $Mg^{2+}$, $Ga^{3+}$, $Tb^{3+}$, $La^{3+}$, $Pb^{2+}$, $Hg^{2+}$, $Cd^{2+}$, $Cu^{2+}$, $Ni^{2+}$, $Co^{2+}$, $Fe^{2+}$, $Mn^{2+}$, $Ba^{2+}$, or $Sr^{2+}$.

9. A kit for binding a metal ion in a sample, comprising at least one metal binding compound of claim 1 and instructions for use thereof.

10. The kit of claim 9, wherein the kit independently further comprises one or more components selected from the group consisting of a calibration standard of a metal ion, an ionophore, a metal ion indicator other than for calcium ions, a detectable signal standard, an aqueous buffer solution, an antibody or fragment thereof, a reference dye standard and an organic solvent.

11. A compound for the detection of metal ions, wherein the compound comprises:
a metal chelating BAPTA moiety; and
a fluorescent protein that is covalently bonded to the metal chelating moiety by a linker,
—$(CR_2)_n NR'$—, wherein R and R' are independently hydrogen, alkyl, or substituted alkyl and n is 1-10;

or —$(CR_2)_n$— wherein R is alkyl or substituted alkyl and n=1-10;

or $(CH_2)_p$ wherein p is 2-10.

12. The compound of claim 11 wherein the metal ion is a calcium ion.

\* \* \* \* \*